(12) United States Patent
Zeller et al.

(10) Patent No.: US 7,183,446 B2
(45) Date of Patent: Feb. 27, 2007

(54) ALCOHOL MIXTURES HAVING 13 AND 15 CARBON ATOMS AND THE USE THEREOF IN THE PREPARATION OF SURFACE-ACTIVE SUBSTANCES

(75) Inventors: Edgar Zeller, Mannheim (DE); Jürgen Tropsch, Römerberg (DE)

(73) Assignee: BASF Aktiengesellschaft, Ludwigshafen (DE)

(*) Notice: Subject to any disclaimer, the term of this patent is extended or adjusted under 35 U.S.C. 154(b) by 818 days.

(21) Appl. No.: 10/311,583

(22) PCT Filed: Jun. 25, 2001

(86) PCT No.: PCT/EP01/07220

§ 371 (c)(1),
(2), (4) Date: Dec. 18, 2002

(87) PCT Pub. No.: WO02/00580

PCT Pub. Date: Jan. 3, 2002

(65) Prior Publication Data

US 2004/0030200 A1    Feb. 12, 2004

(30) Foreign Application Priority Data

Jun. 26, 2000  (DE) ............................... 100 31 107

(51) Int. Cl.
*C07C 29/04* (2006.01)
*C07C 29/03* (2006.01)
*C07C 29/74* (2006.01)
*C07C 29/76* (2006.01)
*C07C 29/36* (2006.01)
*C07C 29/32* (2006.01)

(52) U.S. Cl. .................. 568/876; 568/895; 568/909; 568/913; 514/724

(58) Field of Classification Search ............... 514/724; 568/909, 876, 895, 913
See application file for complete search history.

(56) References Cited

U.S. PATENT DOCUMENTS

| 4,322,545 A | 3/1982 | Scala, Jr. |
| 5,072,057 A | 12/1991 | Oswald et al. |
| 5,849,960 A | 12/1998 | Singleton et al. |
| 6,310,261 B1 | 10/2001 | Geissler et al. |

FOREIGN PATENT DOCUMENTS

| CA | 2132673 | 3/1995 |
| EP | 59 043 | 9/1982 |
| EP | 627 439 | 12/1994 |
| WO | 98/23566 | 6/1998 |

OTHER PUBLICATIONS

Kosswig/Stache, "Die Tenside", Carl Hanser Verlag, Muenchen, Wien, 1993, Kapitel 2.2 und 2.3.
Beller et al., J.Molecular Catalysis A104(1995), S. 17-85.

*Primary Examiner*—Elvis O. Price
(74) *Attorney, Agent, or Firm*—Novak Druce & Quigg LLP

(57) ABSTRACT

The present invention relates to an alcohol mixture which substantively comprises alcohols having 13 or 15 carbon atoms, to a process for its preparation, to a process for functionalizing these alcohol mixtures, and to the resultant functionalized alcohol mixtures and their use.

18 Claims, 1 Drawing Sheet

Fig. 1: Viscosity of $C_{13}-C_{15}$ alcohol + 7 mol of ethylene oxide
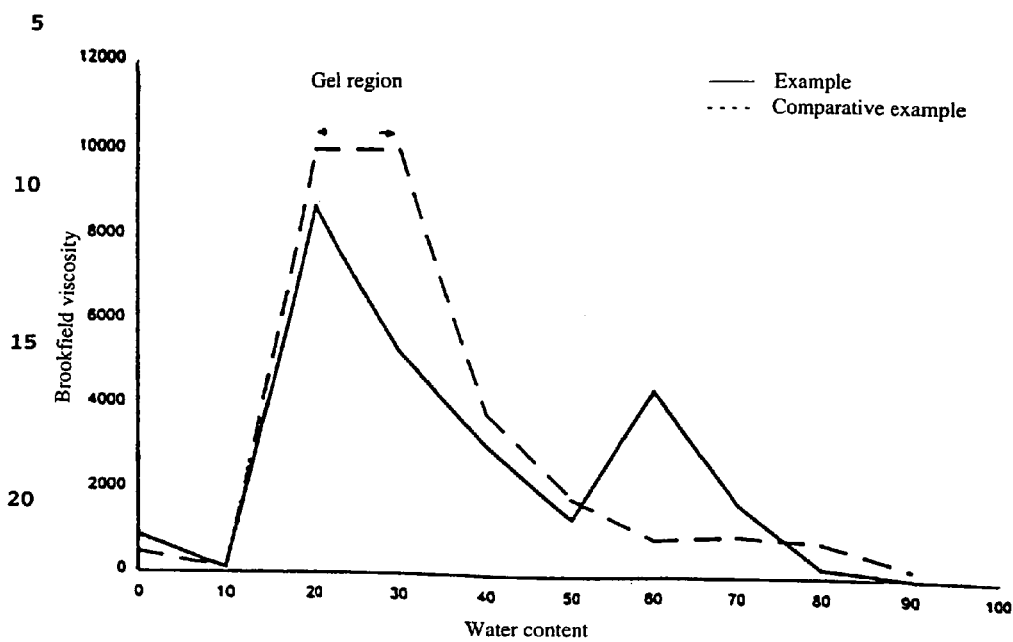
Fig. 2: Viscosity of $C_{13}-C_{15}$ alcohol + 11 mol of ethylene oxide
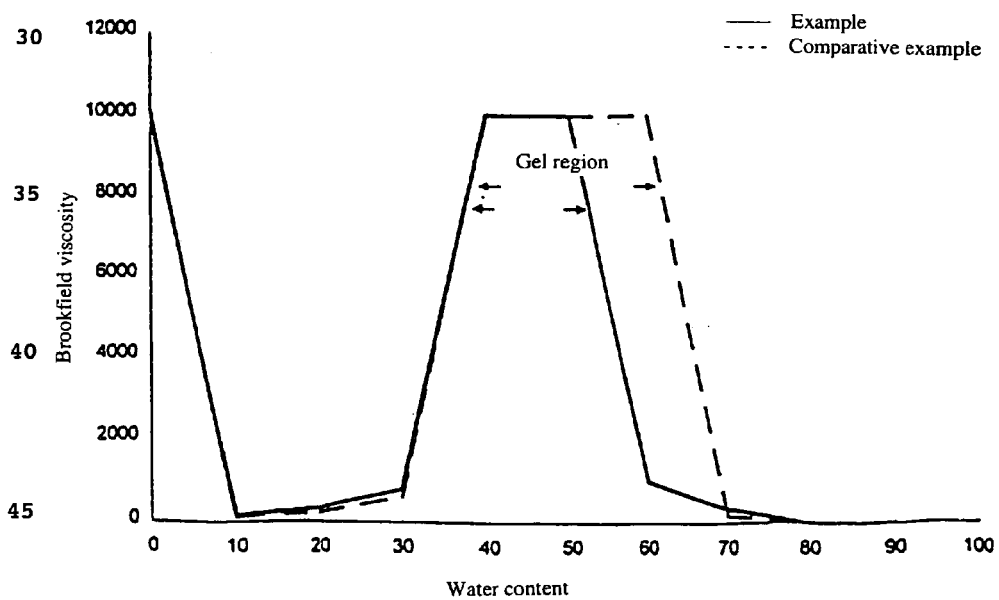

ALCOHOL MIXTURES HAVING 13 AND 15 CARBON ATOMS AND THE USE THEREOF IN THE PREPARATION OF SURFACE-ACTIVE SUBSTANCES

The present invention relates to an alcohol mixture substantively comprising alcohols having 13 or 15 carbon atoms, to a process for its preparation, to a process for functionalizing these alcohol mixtures, and to the resultant functionalized alcohol mixtures and their use.

It is known that fatty alcohols having from 8 to 20 carbon atoms can be used to prepare nonionic or anionic surfactants. For this, the alcohols are subjected to an appropriate functionalization, e.g. alkoxylation or glycosidation. The resulting alkoxylates may either be used directly as nonionic surface-active substances or converted into anionic surface-active substances by another functionalization, e.g. by sulfation or phosphation. The performance characteristics of these surfactants, e.g. their wetting power, foaming, fat-removal power, biodegradability, etc., are determined inter alia by the chain length and the degree of branching of the hydrophilic hydrocarbon radical of the alcohol used. Alcohols highly suitable for further processing to give effective surfactants are also termed surfactant alcohols.

Kosswig/Stache, "Die Tenside", Carl Hanser Verlag, Munich, Vienna, 1993, Chapter 2.2 and 2.3, describes the reaction of fatty alcohols with alkylene oxides to give the corresponding fatty alcohol alkoxylates, and also their sulfation and phosphation.

Surfactant alcohols can be obtained either from natural sources or else by synthesis, e.g. by hydrogenation of natural fatty acids or by building the compounds up from starting materials having a lower number of carbon atoms. For example, linear primary alcohols, "Ziegler alcohols", are obtained from a molecular-weight-increasing reaction of ethene in the presence of triethylaluminium. Another important process, the SHOP process (Shell higher olefin process) starts from ethene to give olefin fractions with a carbon number suitable for further processing to give surfactants. These olefins are functionalized, e.g. by hydroformylation and hydrogenation, to give the corresponding alcohols. An overview of hydroformylation reactions and suitable catalysts is found in Beller et al. Journal of Molecular Catalysis A 104 (1995), pp. 17–85. The result here, even when linear olefins are used, is generally a mixture of straight-chain and branched primary alcohols.

The performance characteristics of these conventional surfactant alcohols, in particular their biodegradability, need further improvement.

WO-A 98/23556 describes a composition of branched primary alcohols and their sulfates, alkoxylates, alkoxysulfates, and carboxylates, which are claimed to have good cold-water washing properties and good biodegradability. These compositions have alcohols having from 8 to 36 carbon atoms, and they have an average degree of branching in the range of from 0.7 to 3.0 per molecule, the branches encompassing methyl branches and ethyl branches. The performance characteristics of these alcohol compositions also need improvement.

It is an object of the present invention to provide a novel alcohol mixture which is advantageously suitable for use as a surfactant alcohol mixture. The anionic and/or nonionic surfactants based on this mixture should also have good performance characteristics, such as good biodegradability, low foaming, or a gel region restricted to a very small range of concentration. A further object of the invention is to provide a process for preparing these alcohol mixtures.

We have found that this object is achieved, surprisingly, by means of an alcohol mixture substantively comprising alcohols having 13 or 15 carbon atoms, where at least 87% by weight of the alcohols have been selected among linear alcohols or among 2-alkyl-branched alcohols.

The invention therefore provides an alcohol mixture which substantively comprises alcohols having 13 or 15 carbon atoms, where, based on the total alcohol content, at least 87% by weight of the alcohols have been selected among linear, 2-methyl-branched, or 2-ethyl-branched alcohols.

For the purposes of the present invention, an alcohol mixture is a mixture which has at least 2, preferably at least 3, different alcohols.

For the purposes of the present invention, an alcohol mixture which substantively comprises alcohols having 13 or 15 carbon atoms is a mixture in which the total proportion of $C_{13}$ and $C_{15}$ alcohols is preferably at least 95% by weight, in particular at least 98% by weight.

The alcohol mixture of the invention is preferably a mixture of primary alcohols.

Preference is given to an alcohol mixture which comprises from 40 to 60% by weight, particularly preferably from 45 to 55% by weight, of linear alcohols. Particular preference is moreover given to a mixture which comprises from 30 to 40% by weight, particularly preferably from 33 to 37% by weight, of 2-methyl-branched alcohols. Preference is, furthermore, given to an alcohol mixture which comprises from 2 to 7% by weight, particularly preferably from 4 to 5.5% by weight, of 2-ethyl-branched alcohols.

The alcohol mixtures of the invention may also comprise other alcohols differing from the abovementioned alcohols, e.g. alcohols with longer-chain branches at the C(2) atom, alcohols with branches at an atom other than the C(2) atom, or alcohols having more than one branch point. All of these are referred to below by the term "alcohols with higher levels of branching".

Preference is given to alcohol mixtures in which the ratio of alcohols having 13 carbon atoms to alcohols having 15 carbon atoms is in the range from 90:10 to 50:50 by weight, preferably from 70:30 to 60:40 by weight.

The composition of the alcohol mixtures of the invention may be determined by conventional methods known to the skilled worker, e.g. gas chromatography. A suitable gas-chromatographic analysis method encompasses the separation of the alcohol mixture on a suitable column, isothermically or by means of a temperature program, detection of the signals by a suitable detector, e.g. a flame ionization, thermal conductivity, or electron capture detector, attribution of the signals to the individual compounds, e.g. by comparison with the retention times of the corresponding pure alcohols (where appropriate after addition of an internal standard), and integration of the signal areas to determine the proportions by weight of the individual alcohols in the mixture.

The alcohol mixtures of the invention preferably have an average degree of branching of not more than 0.65, preferably not more than 0.5.

The degree of branching is defined as the number of methyl groups in one molecule of the alcohol minus 1. The average degree of branching is the statistical average of the degrees of branching in a specimen. The average number of methyl groups in the molecules of a specimen may readily be determined by $^1$H NMR spectroscopy. For this, the signal area corresponding to the methyl protons is divided by three and related to the signal area of the methylene protons of the $CH_2OH$ group, divided by two. The average degree of branching may also be determined by computer methods from the composition of the alcohol mixture as determined by gas chromatography.

The alcohol mixtures of the invention are advantageously suitable for functionalization to prepare surface-active mixtures. These generally and advantageously have better performance characteristics than alcohol mixtures known from the prior art, e.g. better biodegradability, reduced foaming, or improved gelling behavior.

The present invention also provides a process for preparing alcohol mixtures as described above, where:
a) a monoolefin mixture is prepared, substantively comprising olefins having 12 or 14 carbon atoms and having linear α-olefins and from 5 to 20% by weight of olefins other than these, and
b) the monoolefin mixture is hydroformylated by reaction with carbon monooxide and hydrogen in the presence of a rhodium catalyst, and is hydrogenated.

Step a)

The process of the invention preferably uses a monoolefin mixture produced on an industrial scale.

Examples of these are the Ziegler olefins obtained by controlled oligomerization of ethene in the presence of alkylaluminum catalysts. They also include the olefins obtained by oligomerization of ethene in the presence of various catalyst systems, e.g. the olefins obtained in the presence of alkylaluminum chloride/titanium tetrachloride catalysts, or in the presence of nickel-phosphine complex catalysts using the Shell Higher Olefin Process (SHOP). Other suitable industrially accessible olefin mixtures are obtained in the paraffin-dehydrogenation of appropriate mineral oil fractions, e.g. of what are known as the petroleum or diesel oil fractions. There are three processes of which substantive use is made for converting paraffins, mainly n-paraffins, into olefins:
  thermal cracking (steam-cracking),
  catalytic dehydrogenation, and
  chemical dehydrogenation via chlorination and dehydrochlorination.

Thermal cracking here leads mainly to α-olefins, whereas the other techniques give olefin mixtures which generally include olefins having a non-terminal double bond. Other suitable olefin mixtures are the olefins obtained in metathesis reactions or telomerization reactions. Examples of these are the olefins from the Philipps triolefin process, a modified SHOP process comprising ethylene oligomerization, double-bond isomerization, and subsequent metathesis (etheneolysis). Other processes for preparing suitable olefins are the preparation of α,ω-diolefins by ring-opening etheneolysis of cycloolefins, the metathesis polymerization of cycloolefins to give polyalkeneamers with subsequent etheneolysis, etc. Etheneolysis generally gives a high concentration of n-α-olefins.

Industrially accessible monoolefin mixtures of olefins having 12 carbon atoms and olefins having 14 carbon atoms are also called $C_{12}$–$C_{14}$ olefins. Preference is given to mixtures in which the ratio of olefins having 12 carbon atoms to olefins having 14 carbon atoms is in the range from 90:10 to 50:50 by weight, preferably from 70:30 to 60:40 by weight. Particular preference is given to $C_{12}$–$C_{14}$ olefins in which the ratio of mixing of the olefins is in the region of about 2:1.

The process of the invention is advantageously suitable for preparing alcohol mixtures from industrially accessible monoolefin mixtures which generally comprise not only linear α-olefins but also olefins having non-terminal double bonds and branched olefins. The process of the invention is therefore more cost-effective than prior art processes which are dependent on the use of linear α-olefins, or in which olefins other than linear α-olefins are not converted into useful products. Suitable industrial monoolefin mixtures generally have up to 15% by weight of olefins other than α-olefins. These include not only olefins having non-terminal double bonds but also vinylidene-branched olefins which have a group of the formula (—C($R^a$)=$CH_2$), where $R^a$ is alkyl, preferably $C_1$–$C_6$-alkyl, in particular methyl or ethyl. Examples of processes which give vinylidene-branched olefin isomers of this type are the dimerization of low-molecular-weight olefin cuts or the incorporation of higher n-1-olefins during ethene oligomerization in the Ziegler process.

The process of the invention preferably uses a monoolefin mixture which, based on the total olefin content, comprises from 85 to 95% by weight of linear α-olefins, from 1 to 5% by weight of linear non-terminal olefins, from 5 to 10% by weight of vinylidene-branched olefins, and, where appropriate, up to 5% by weight of other olefin isomers differing therefrom. These other olefin isomers include, for example, isomers which have more than one branching point, and isomers having a longer-chain vinylidene branch.

Surprisingly, even when use is made of industrially accessible monoolefin mixtures, the process of the invention gives alcohol mixtures which when used as surfactant alcohol mixtures have advantageous performance characteristics.

Step b)

BRIEF DESCRIPTION OF THE DRAWINGS

FIGS. 1 and 2 are viscosity diagramas of $C_{13}$–$C_{15}$ alcohol plus ethylene oxide.

The hydroformylation in step b) takes place under conditions in which it is not only the linear α-olefins which are hydroformylated but essentially all of the olefins in the monoolefin mixture used.

According to the invention, a rhodium catalyst is used for the hydroformylation in step b). The rhodium catalysts used are preferably not rhodium/triarylphosphine catalysts, e.g. rhodium/triphenylphosphine catalysts, or catalysts based on ligands which have similar stearic and electronic properties, such as triarylphosphine. Catalysts of this type are generally suitable only for converting n–1-olefins or the n–1-olefin content of olefin mixtures.

The rhodium catalysts used for the hydroformylation in step b) derive from conventional rhodium complexes or salts known to the skilled worker, as usually used in hydroformylation reactions. The ligands preferably used here enable the catalyst, under the reaction conditions, to catalyze both the hydroformylation of linear α-olefins and that of olefins having non-terminal double bonds and/or that of branched olefins. The catalyst used in step b) preferably has at least one ligand selected among compounds capable of forming complexes and having carbonyl, carboxylate, hydride, sulfate, or nitrate groups, or having nitrogen-containing and/or phosphorus-containing groups, where the phosphorus-containing group has no more than one aryl radical with single bonding to the phosphorus atom.

Suitable rhodium catalysts or rhodium catalyst precursors are rhodium(II) salts and rhodium(III) salts, such as rhodium (III) chloride, rhodium(III) nitrate, rhodium(III) sulfate, potassium rhodium sulfate (rhodium alum), rhodium(II) carboxylate, rhodium(III) carboxylate, preferably rhodium (II) acetate or rhodium(III) acetate, rhodium(II) ethylhexanoate or rhodium(III) ethylhexanoate, rhodium(III) oxide, salts of rhodium(III) acid, and trisammonium hexachlororhodate(III).

Other suitable rhodium catalysts are rhodium complexes of the formula $RhX_mL^1L^2(L^3)_n$, where X is halide, preferably chloride, or bromide, alkyl carboxylate, aryl carboxylate, acetylacetonate, arylsulfonate or alkylsulfonate, in particular phenylsulfonate or toluenesulfonate, hydride or the diphenyltriazine anion, and $L^1$, $L^2$, and $L^3$, independently of one another, are CO, olefins, cycloolefins, preferably cyclooctadiene (COD). X is preferably hydride, chloride, bromide, acetate, tosylate, acetylacetonate, or the diphenyltriazine anion, in particular hydride, chloride or acetate.

In one first preferred embodiment, the process of the invention uses a rhodium catalyst which has at least one unbridged phosphacyclohexane structural unit and/or unbridged phosphacyclohexene structural unit as ligand.

The catalyst preferably has, as ligand, at least one phosphacyclohexane of the formulae I and II

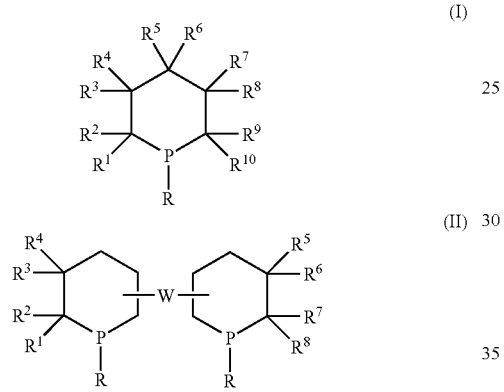

where

R is hydrogen, C1-100-alkyl, cycloalkyl, heterocycloalkyl, $C_{7-20}$-aralkyl, $C_{7-20}$-alkaryl, $C_{6-12}$-aryl, hetaryl, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', or W'COR', where in formula II the radicals R may also, instead of or in addition to the group W, together form a bridge having from 1 to 20 carbon atoms, which may be a constituent of a cyclic or aromatic group and may have interruption by heteroatoms, and where in formula II the radicals R may also, instead of or in addition to the group W, together be a polyoxyalkylene bridge or polyalkyleneimine bridge having at least 21 carbon atoms, $R^1$ to $R^{10}$ independently of one another are hydrogen, $C_{1-20}$-alkyl, $C_{7-20}$-aralkyl, $C_{7-20}$-alkaryl, $C_{6-12}$-aryl, where one or more carbon atoms may have been replaced by heteroatoms, W'COO$^-$M$^+$, W'SO$_3^-$M$^+$, W'PO$_3^{2-}$M$^+_2$, W'NR'$_3^+$X$^-$, W'OR', W'NR$_2$, W'COOR', W'SR', W'(CHR'CH$_2$O)$_x$ R', W'(CH$_2$NR')$_x$R', W'(CH$_2$CH$_2$NR')$_x$R', W'((CH$_2$)$_4$O)$_x$R', W'halogen, W'NO$_2$, W'COR' or W'CN, where one or more hydrogen atoms in radicals R and $R^1$ to $R^{10}$ may have been replaced by fluorine, W and W' independently of one another are single bonds or bridges having from 1 to 20 carbon atoms, which may be a constituent of a cyclic or aromatic group and which may have interruption by heteroatoms, where W may also be a polyoxyalkylene or polyalkyleneimine bridge having at least 21 carbon atoms, R' is hydrogen, $C_{1-20}$-alkyl, carbonylalkyl, cycloalkyl or aryl, M$^+$ is a cation equivalent, X$^-$ is an anion equivalent, and x is an integer from 1 to 240, where two geminal radicals $R^1$ to $R^{10}$ may form an oxo group, and one or more of the radicals R and $R^1$ to R10 may have an additional triply bonded phosphorus-containing or nitrogen-containing group capable of coordination, and where any two vicinal radicals may have bonding to give anellated, aliphatic or aromatic rings, and where two vicinal radicals $R^1$ to $R^{10}$ may also be a chemical bond, and where in the compounds of the general formula II there may also be two or more bridges W present, and where those atoms of the phosphacyclohexane rings not bonded to the bridge(s) W may also have substitution as defined for $R^1$ to $R^{10}$, and where in the compounds of the formula I, one of the radicals R or $R^1$ to $R^{10}$, and in the compounds of the formula II one of the radicals R or $R^1$ to $R^8$ or the two radicals R together or a group W may also be a polymer radical with a number-average molecular weight in the range from 500 to 50 000, composed of repeat units which derive from monomers selected from mono- and diolefins, vinylaromatics, esters of α,β-ethylenically unsaturated mono- or dicarboxylic acids with $C_1$–$C_{30}$ alkanols, N-vinylamides, N-vinyllactams, heterocyclic compounds polymerizable with ring-opening, and mixtures of these.

For the purposes of the present invention, the expression "alkyl" encompasses straight-chain and branched alkyl groups. These are preferably straight-chain or branched $C_1$–$C_{100}$-alkyl groups, with preference $C_1$–$C_{20}$-alkyl groups, and particularly preferably $C_1$–$C_{10}$-alkyl groups, and very particularly preferably $C_1$–$C_4$-alkyl groups. Examples of alkyl groups are in particular methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl, nonyl, decyl.

Substituted alkyl radicals preferably have 1, 2, 3, 4, or 5, in particular 1, 2, or 3, substituents. Examples of these are selected from cycloalkyl, aryl, hetaryl, halogen, NE$^1$E$^2$, (NE$^1$E$^2$E$^3$)$^+$, carboxy, carboxylate, —SO$_3$H, and sulfonate.

The cycloalkyl group is preferably a $C_5$–$C_7$-cycloalkyl group, such as cyclopentyl, cyclohexyl, or cycloheptyl.

The heterocycloalkyl group is preferably a $C_{5-7}$-heterocycloalkyl group. The heterocycloalkyl group preferably has 1, 2, 3, or 4 unsubstituted or substituted heteroatoms. Examples of these are pyrrolidine, tetrahydrofuran, pyrazolidine, imidazolidine, piperidine, piperazine, and morpholine.

If the cycloalkyl group or heterocycloalkyl group has substitution, it preferably has 1, 2, 3, 4, or 5, in particular 1, 2, or 3, substituents, selected from alkyl, alkoxy, and halogen.

Aryl is preferably phenyl, tolyl, xylyl, mesityl, naphthyl, anthracenyl, phenanthrenyl, naphthacenyl, and in particular phenyl, naphthyl, or xylyl.

Substituted aryl radicals preferably have 1, 2, 3, 4, or 5, in particular 1, 2, or 3, substituents, selected from alkyl, alkoxy, carboxy, carboxylate, trifluoromethyl, —$SO_3H$, sulfonate, $NE^1E^2$, alkylene-$NE^1E^2$, nitro, cyano, and halogen.

Hetaryl is preferably pyrrolyl, pyrazolyl, imidazolyl, indolyl, carbazolyl, pyridyl, quinolinyl, acridinyl, pyridazinyl, pyrimidinyl, or pyrazinyl.

Substituted hetaryl radicals preferably have 1, 2, or 3 substituents, selected from alkyl, alkoxy, carboxy, carboxylate, —$SO_3H$, sulfonate, $NE^1E^2$, alkylene-$NE^1E^2$, trifluoromethyl, and halogen.

The above descriptions of alkyl, cycloalkyl, and aryl radicals apply correspondingly to alkoxy, cycloalkyloxy, and aryloxy radicals.

$E^1$, $E^2$, and $E^3$ have preferably been selected independently from hydrogen, alkyl, and cycloalkyl. The radicals $NE^1E^2$ are preferably N,N-dimethyl, N,N-diethyl, N,N-dipropyl, N,N-diisopropyl, N,N-di-n-butyl, N,N-di-tert-butyl, N,N-dicyclohexyl, and N,N-diphenyl.

Heteroatom is preferably an oxygen, sulfur, disubstituted silicon or monosubstituted nitrogen atom, where the substituents, independently of one another, are hydrogen, alkyl, cycloalkyl, heterocycloalkyl, aryl, hetaryl, alkoxy, cycloalkoxy, or aryloxy.

Halogen is fluorine, chlorine, bromine, or iodine, preferably fluorine, chlorine, or bromine.

For the purposes of this invention, carboxylate and sulfonate are preferably a derivative of a carboxylic acid function or of a sulfonic acid function, in particular a metal carboxylate or metal sulfonate, a carboxylic ester function or sulfonic ester function, or a carboxamide function or sulfonamide function. Examples of these are the esters with $C_1$–$C_4$ alkanols, such as methanol, ethanol, n-propanol, isopropanol, n-butanol, sec-butanol, and tert-butanol.

For the purposes of this invention, polybutadienes include their products of partial or complete hydrogenation.

Polyoxyalkylene is preferably compounds having repeat units selected from $-(CH_2CH_2O)_{\overline{x1}}$, $-(CH(CH_3)CH_2O)_{\overline{x2}}$ and $-((CH_2)_4O)_{\overline{x3}}$, where $x_1$, $x_2$, and $x_3$, independently of one another, are an integer from 0 to 240, preferably from 0 to 100. The total of $x_1$, $x_2$, and $x_3$ is an integer from 1 to 240, preferably from 2 to 100. In polyoxyalkylenes which have two or three different repeat units, the sequence is as desired, i.e. the repeat units may have random distribution, or be alternate or form blocks. The above description of the polyoxyalkylenes apply similarly to polyalkyleneimines, each oxygen atom having been replaced by an $NR^i$ group, where $R^i$ is hydrogen or $C_{1-4}$-alkyl.

$M^+$ is a cation equivalent, i.e. a monovalent cation or that portion of a polyvalent cation which corresponds to a single positive charge. $M^+$ is preferably an alkali metal cation, e.g. $Li^+$, $Na^+$, or $K^+$, or an alkaline earth metal cation, $NH_4^+$, or a quaternary ammonium compound, as can be obtained by protonation or quaternization of amines. Alkali metal cations are preferred, in particular sodium ions or potassium ions.

$X^-$ is an anion equivalent, i.e. a monovalent anion or that portion of a polyvalent anion which corresponds to a single negative charge. $X^-$ is preferably a carbonate, carboxylate, or halide, particularly preferably $Cl^-$ or $Br^-$.

The values for x are an integer from 1 to 240, preferably an integer from 1 to 100, in particular from 1 to 50, specifically from 3 to 40.

If the radical R is a substituted $C_{1-100}$-alkyl radical, this may have mono- or polysubstitution by radicals as given for $R^1$ to $R^{10}$.

One or more of the carbon atoms present in the radicals R may have been replaced by heteroatoms.

The radical R has preferably been selected from phenyl radicals or $C_{1-12}$-alkyl radicals, and these may be linear, branched, or cyclic alkyl radicals, which may also contain oxygen atoms as heteroatoms in the chain, e.g. in the form of alkylene oxide units, in particular ethylene oxide units, which may have been terminally alkylated.

The radical R is preferably a $C_{2-14}$-alkyl radical, in particular propyl, n-butyl, sec-butyl, tert-butyl, pentyl, hexyl, heptyl, octyl, 2-ethylhexyl, or dodecyl.

Another preferred meaning of the radical R is a $C_{5-8}$-cycloalkyl radical, in particular cyclohexyl.

Another preferred meaning of the radical R is a polyoxyalkylene radical or polyalkyleneimine radical. Examples of compounds from which suitable polyoxyalkylenes derive are formaldehyde (polyoxymethylenes), cyclic ethers, such as tetrahydrofuran, alkylene oxides having from 2 to 4 carbon atoms in the alkyl radical, and combinations of these. Examples of suitable alkylene oxides are ethylene oxide, propylene 1,2-oxide, epichlorohydrin, butylene 1,2- and 2,3-oxide. Examples of compounds from which suitable polyalkyleneimines derive are aziridines (alkyleneimines) of the formula

where $R^\alpha$ is hydrogen or alkyl. The number-average molecular weight of the polyoxyalkylene radicals or polyalkyleneimine radicals is preferably in the range from about 400 to 50 000, particularly preferably from 800 to 20 000, specifically from 2 000 to 10 000. If a substituent has two or more radicals R, these may be identical or different.

The structures of the formulae I and II may be phosphacyclohexanones if two geminal radicals selected from R1 to $R^{10}$ represent =O. In this instance $R^5$ and $R^6$ in formula I preferably represent a double-bonded oxygen atom.

In the phosphacyclohexanes of the formulae I and II, at least two or three or four of the radicals $R^1$ to $R^{10}$ are preferably not hydrogen. At least one, two, or three of the radicals R and $R^1$ to $R^{10}$ preferably contain cyclic structures which may be aliphatic, aromatic, or heterocyclic. In the compounds of the formula I, examples of positions in which the cyclic structures are found are positions 2, 4, and 6. The structures may also be found in positions 1, 2, and 6, for example.

The radicals $R^1$ to $R^{10}$ are preferably hydrogen and radicals as defined for R, in particular $C_{1-12}$-alkyl radicals, $C_{7-13}$-aralkyl radicals, $C_{7-13}$-alkaryl radicals, and/or $C_{6-12}$-aryl radicals. The alkyl radicals may contain cyclic structures. The aryl groups of the aralkyl radicals, alkaryl radicals, and aryl radicals preferably derive from benzene or naphthalene. The radicals ($R^1$ to $R^{10}$) may therefore be phenyl radicals or naphthyl radicals. Alkaryl radicals here preferably have one, two, or three alkyl substituents, which are in particular methyl or ethyl radicals.

If R and/or $R^1$ to $R^{10}$ are alkyl and aryl radicals, these may have been fluorinated or perfluorinated. A preferred fluorinated alkyl radical is trifluoromethyl.

In one suitable embodiment of the invention, at least one of the radicals R or $R^1$ to $R^{10}$ in the compounds of the formula I or II is a polar (hydrophilic) group, the resultant catalysts then generally being water-soluble. Preference is given to polar groups selected from W'COO$^-$M$^+$, W'SO$_3^-$ M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', and W'((CH$_2$)$_4$O)$_x$R', where W', M$^+$, X$^-$, x, and R' are as defined above.

At least one of the substituents R and $R^1$ to $R^{10}$ may have an additional trivalent phosphorus group or trivalent nitrogen group capable of coordination, giving a bi- or polydentate ligand. Particular preference is given to phosphane groups, phosphinite groups, phosphonite groups, and phosphite groups, and also $\eta^5$-phospholyl complexes, or phosphabenzene groups.

The radicals $R^1$ to $R^{10}$ are preferably hydrocarbon radicals which have no other heteroatoms.

In one preferred embodiment, the bridges W and W' are single bonds or bridges having from 1 to 6 carbon atoms, which may be a constituent of a cyclic or aromatic group. These may be single bonds or lower alkylene groups, e.g. $C_{1-10}$-alkylene.

In the compounds of the formula II, the two radicals R together and/or a group W may be a bridge having from 1 to 20 carbon atoms, which may be a constituent of a cyclic or aromatic group and/or which may have interruption by heteroatoms. In one first preferred embodiment, the bridging groups are a $C_{1-20}$-alkylene chain. Where appropriate, bridging alkylene chains have substitution by cycloalkyl, heterocycloalkyl, aryl, and/or hetaryl, and these may, where appropriate, bear 1, 2, or 3 of the abovementioned substituents. Depending on the number of carbon atoms in the alkylene chain, bridging alkylene chains may have 1, 2, 3, or 4 double bonds, and/or have interruption by from 1 to 10, e.g. 1, 2, or 3, non-adjacent, where appropriate substituted, heteroatoms, and/or may have been mono-, bi-, or trianellated with cycloalkyl, aryl, or hetaryl. $C_{1-15}$-alkylene chains are preferred, and $C_{1-10}$-alkylene chains are particularly preferred, examples being $C_6$-alkylene or $C_3$-alkylene chains.

If the two radicals R in the compounds of the formula II together and/or a group W are an aryl-anellated alkylene bridge, the anellated aryl systems are preferably benzene or naphthalene.

Anellated benzene rings preferably have no substitution or have one, two, or three, in particular one or two, substituents, selected from alkyl, alkoxy, halogen, SO$_3$H, sulfonate, NE$^1$E$^2$, alkylene-NE$^1$E$^2$, trifluoromethyl, nitro, carboxy, alkoxycarbonyl, acyl, and cyano. Anellated naphthalenes are preferably unsubstituted or have, in the non-anellated ring and/or in the anellated ring, in each case one, two, or three, in particular one or two, of the substituents mentioned above for the anellated benzene rings.

The bridging groups are preferably an unsubstituted $C_{2-6}$-alkylene bridge.

Another preferred meaning for the two radicals R together and/or a group W is a $C_{2-20}$-alkylene bridge which has interruption by up to 20, in particular by up to 10, non-adjacent, where appropriate substituted, heteroatoms. These have preferably been selected from O, S, NR$^\alpha$, and SiR$^\beta$R$^\gamma$, where the radicals R$^\alpha$, R$^\beta$, and R$^\gamma$ are, independently of one another, alkyl, cycloalkyl, or aryl. Preference is given to oligomeric polyoxyalkylene bridges and oligomeric polyalkyleneimine bridges. These have the repeat units described above, for example.

In another embodiment, in the compounds of the formula II, the two radicals R together and/or a group W may also be a relatively high-molecular-weight polyoxyalkylene bridge or relatively high-molecular-weight polyalkyleneimine bridge having at least 21 carbon atoms. The number-average molecular weight of the polyoxyalkylene radicals or polyalkyleneimine radicals is preferably in the range from about 400 to 50 000, particularly preferably from 800 to 20 000, and specifically from 1 000 to 10 000. Particular preference is given here to polyethylene oxides, copolymers of ethylene oxides and propylene 1,2-oxide where the alkylene oxides may have been incorporated in any desired sequence, alternating, or in block form, and also to polyethyleneimines.

In one suitable embodiment, in the compounds of the formula I, one of the radicals R or $R^1$ to $R^{10}$ may also be, in the compounds of the formula II one of the radicals R or $R^1$ to $R^8$ or the two radicals R together may also be, or a group W may also be, a polymer radical with a number-average molecular weight in the range from about 500 to 50 000, differing from the definitions given above for these radicals and groups. The repeat units of these polymer radicals formally derive from monomers selected from mono- and diolefins, vinylaromatics, esters of $\alpha,\beta$-ethylenically unsaturated mono- or dicarboxylic acids with $C_1$–$C_{30}$ alkanols, N-vinylamides, N-vinyllactams, heterocyclic compounds which can be polymerized with ring-opening, and mixtures of these.

The polymer radicals preferably have a number-average molecular weight in the range from 800 to 20 000, particularly preferably from 2 000 to 10 000.

Monoolefins preferred as monomers are $C_{2-8}$ monoolefins, such as ethene, propene, n-butene, isobutene, and aromatic-substituted monoolefins, such as 1,1-diphenylethylene, 1,2-diphenylethylene, and mixtures of the abovementioned monoolefins. Diolefins preferred as monomers are conjugated dienes, such as butadiene, isoprene, 2,3-dimethylbutadiene, piperylene(1,3-pentadiene), and mixtures of these. The esters of $\alpha,\beta$-ethylenically unsaturated mono- or dicarboxylic acids have preferably been selected from the esters of acrylic acid, methacrylic acid, maleic acid, fumaric acid, itaconic acid, or crotonic acid. Preference is given to the esters with $C_{1-20}$ alkanols. These include, for example, methyl (meth)acrylate, ethyl (meth)acrylate, n-butyl (meth)acrylate, tert-butyl (meth)acrylate, n-hexyl (meth)acrylate, n-octyl (meth)acrylate, ethylhexyl (meth)acrylate, etc. Examples of vinylaromatics suitable as monomers are styrene, $\alpha$-methylstyrene, o-chlorostyrene, vinyltoluenes, and mixtures of these. Examples of suitable N-vinylamides are N-vinylformamide, N-vinylacetamide, N-vinylpropionamide, and mixtures of these. Examples of suitable N-vinyllactams are N-vinylpyrrolidone, N-vinylpiperidone, N-vinylcaprolactam, and mixtures of these. Examples of monomers suitable for ring-opening polymerization are cyclic ethers, such as ethylene oxide and propylene oxide, cyclic amines, cyclic sulfides (ethylene sulfide, thietanes), lactones, and lactams. Preference is given to $\epsilon$-caprolactone and $\epsilon$-caprolactam.

The abovementioned monomers may be used individually, in the form of mixtures derived from each class of monomer, or else in the form of mixtures generally.

The polymers suitable as radicals are prepared by conventional polymerization processes known to the skilled worker. Depending on the monomers to be polymerized, these include free-radical, cationic, and anionic polymerization, including cationic and anionic ring-opening polymerization.

The polymer radicals are prepared by anionic polymerization, for example by the appropriate version described below of a reaction to prepare the phosphacyclohexanes of the invention, the monomers used preferably comprise acceptor-activated ethylenically unsaturated compounds and ethene.

If, in the compounds of the formula I, one of the radicals R or $R^1$ to $R^{10}$ is a polymer radical, and if, in the compounds of the formula II, one of the radicals R or $R^1$ to $R^8$ is a polymer radical, or if the two radicals R together or a group W is/are a polymer radical, preference is given to a polyolefin radical (polyalkene radical). These polyolefins have repeat units which derive from monomers incorporated in the polymer and preferably selected from $C_{2-6}$ alkenes, such as ethene, propene, n-butene, isobutene, olefins having two double bonds, such as butadiene, isoprene, 1,3-pentadiene, and mixtures of these. Polyolefins which incorporate conjugated dienes may contain substantially only the 1,2 and 1,4 polymerization products, or else contain mixed forms with any desired proportions of 1,2 and 1,4. Processes for adjusting the 1,2 and 1,4 proportions during the polymerization of conjugated dienes are known to the skilled worker. Examples of these include, for anionic polymerization, the addition of donor solvents, e.g. ethers, such as THF, or of amines. Polyolefins having repeat units of 1,2 addition products of conjugated dienes have ethylenically unsaturated side groups. Polyolefins having repeat units of 1,4 addition products have ethylenically unsaturated groups in the main chain. If desired, some or all of these may be hydrogenated. However, phosphacyclohexanes having polyolefin radicals having ethylenically unsaturated side chains may also be used as ligands in the transition metal complexes for hydroformylation. In this case, under hydroformylation conditions there is generally at least some reaction of the ethylenically unsaturated side chains to give alcohol groups, i.e. ligands with polar side chains are formed.

If, in the compounds of the formula I, one of the radicals R or $R^1$ to $R^{10}$ is a polyolefin radical, or if, in the compounds of the formula II, one of the radicals R or $R^1$ to $R^8$ is a polyolefin radical, or if the two radicals R together or a group W is/are a polyolefin radical, preference is given to a polyethylene radical or polybutadiene radical.

Those positions on the phosphacyclohexane rings in structure II not bonded to the bridge W may also bear one of the radicals R or $R^1$ to $R^{10}$.

The radical R' is preferably hydrogen or $C_{1-6}$-alkyl, such as a methyl or ethyl radical. If a substituent has two or more radicals R', these may be identical or different.

On each ring carbon atom of the phosphacyclohexane there is preferably, apart from C=O in position 4 and $C(CH_3)_2$ in position 2 and/or position 6, a maximum of one substituent other than hydrogen. For example, there may be substituents in positions 2 and 6, positions 2, 4 and 6, or positions 2, 3, 5, and 6. Particular preference is given to substituents, specifically aryl, in positions 2 and 6.

The ligands used preferably comprise phosphacyclohexanes which have been selected from compounds of the formula III

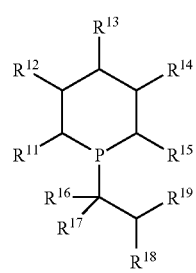

(III)

where:

$R^{11}$ to $R^{19}$, independently of one another, are hydrogen, $C_{1-20}$-alkyl, $C_{7-20}$-aralkyl, $C_{7-20}$-alkaryl, $C_{6-12}$-aryl, where one or more carbon atoms may have been replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$ R', W'(CH$_2$NR')$_x$R', W'(CH$_2$CH$_2$NR')$_x$ R', where any two vicinal radicals R11 to $R^{15}$ and/or $R^{17}$ and $R^{18}$ and/or $R^{16}$ and $R^{17}$, and/or $R^{16}$ and $R^{19}$, and/or $R^{18}$ and $R^{19}$ may have been bonded to give rings, W' is a single bond or bridge having from 1 to 20 carbon atoms, which may be a constituent of a cyclic or aromatic group, R' is hydrogen or $C_{1-6}$-alkyl, $M^+$ is a cation, $X^-$ an anion, x is a number from 1 to 240, where one or more of the radicals $R^{11}$ to $R^{19}$ may have an additional trivalent phosphorus group or nitrogen group capable of coordination, and where $R^{18}$ may also be —W'—CR$^{20}$=CR$^{21}$R$^{22}$, where $R^{20}$, $R^{21}$, $R^{22}$ may be as defined above for R11 to $R^{19}$.

The ligands used particularly preferably comprise phosphacyclohexanes selected from compounds of the formulae I.a to I.g and II.a

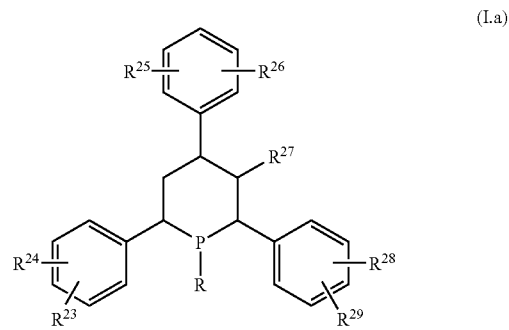

(I.a)

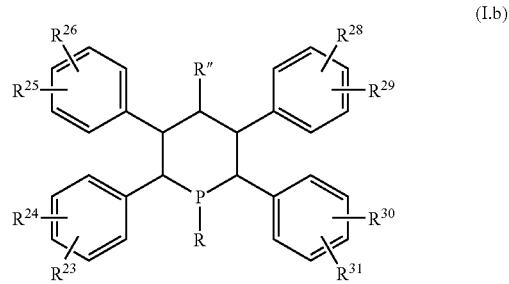

(I.b)

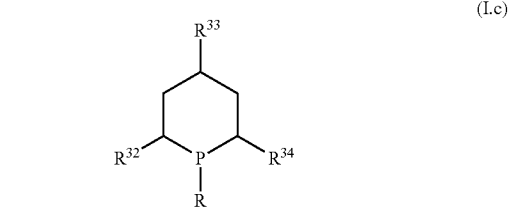

(I.c)

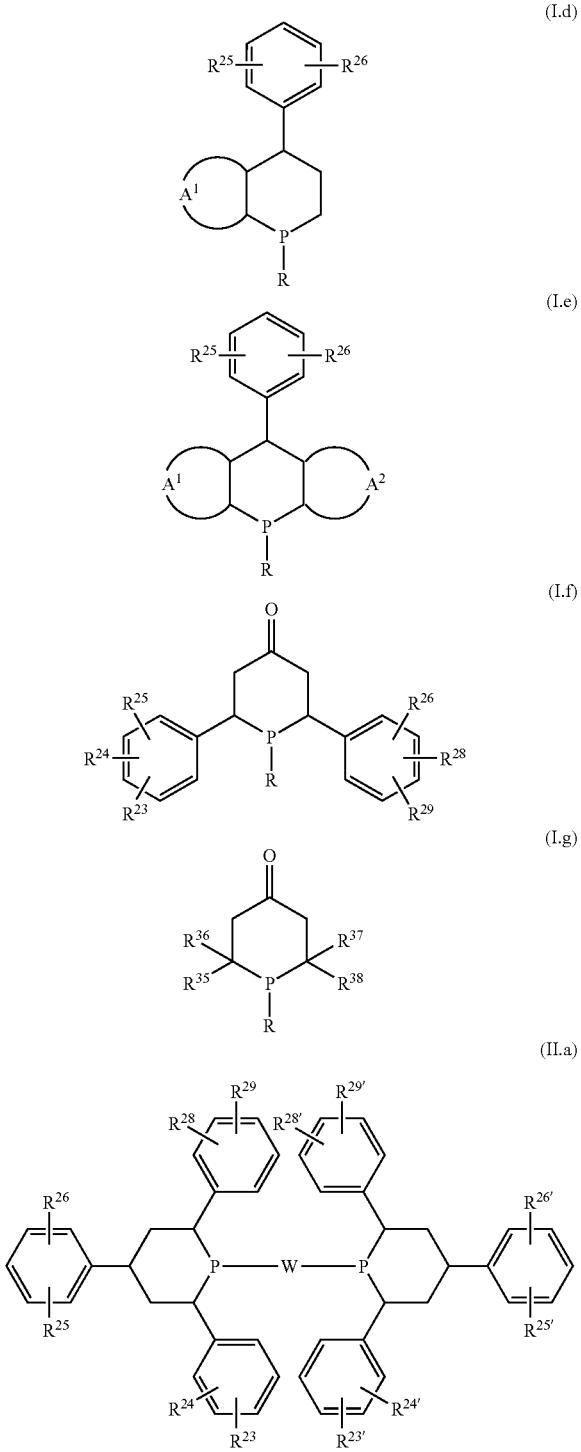

where
R is $C_{1-20}$-alkyl, cycloalkyl, $C_{6-12}$-aryl, W'(CHR'CH$_2$O)$_n$R', W'((CH$_2$)$_4$O)$_x$R', or a polymer radical with number-average molecular weight in the range from 500 to 50 000, composed of ethylene and/or butadiene, where
W' is a single bond or $C_{1-4}$-alkylene, and
R' is hydrogen or $C_{1-20}$-alkyl,
x is an integer from 1 to 240, $R^{23}$, $R^{23'}$, $R^{24}$, $R^{24'}$, $R^{25}$, $R^{25'}$, $R^{26}$, $R^{26'}$, $R^{28}$, $R^{28'}$, $R^{29}$, $R^{29'}$, $R^{30}$, and $R^{31}$, independently of one another, are hydrogen, alkyl, alkoxy, carboxy, carboxylate, trifluoromethyl, —SO$_3$H, sulfonate, NE$^1$E$^2$, or alkylene-NE$^1$E$^2$, where E$^1$ and E$^2$, independently of one another, are hydrogen, alkyl, or cycloalkyl, $R^{27}$ is hydrogen, alkyl, cycloalkyl, aryl, or aralkyl, $R^{32}$, $R^{33}$, $R^{34}$, $R^{35}$, $R^{36}$, $R^{37}$, and $R^{38}$, independently of one another, are alkyl or cycloalkyl, R" is hydrogen or phenyl, A$^1$ and A$^2$, together with those adjacent carbon atoms of the phosphacyclohexane to which they have been bonded, are an anellated ring system in each case having 1 or 2 further rings, W is a bridge having from 1 to 20 carbon atoms, which may have interruption by heteroatoms.

In the compounds of the formula I.a to I.f and II.a, the radicals $R^{23}$, $R^{23'}$, $R^{24}$, $R^{24'}$, $R^{25}$, $R^{25'}$, $R^{26}$, $R^{26'}$, $R^{28}$, $R^{28'}$, $R^{29}$, $R^{29'}$, $R^{30}$, and $R^{31}$ are preferably, independently of one another, hydrogen, $C_{1-4}$-alkyl, preferably methyl, ethyl, isopropyl, tert-butyl, $C_{1-4}$-alkoxy, preferably methoxy.

$R^{27}$ is preferably aralkyl, in particular benzyl.

$R^{32}$, $R^{33}$, and $R^{34}$, independently of one another, are preferably $C_{1-4}$-alkyl, particularly preferably tert-butyl.

$R^{35}$, $R^{36}$, $R^{37}$, and $R^{38}$, independently of one another, are preferably $C_{1-4}$-alkyl, particularly preferably methyl.

The rings of the anellated ring systems A$^1$ and A$^2$ are preferably 5- to 7-membered rings. Preference is given to ring systems which derive from benzene, from naphthalene, or from partially hydrogenated or perhydrogenated products of these. Fused rings preferably have no substitution or have 1, 2, or 3, in particular 1 or 2, substituents per ring, these having being selected from alkyl, alkoxy, halogen, SO$_3$H, sulfonate, NE$^1$E$^2$, alkylene-NE$^1$E$^2$, trifluoromethyl, nitro, carboxy, alkoxycarbonyl, acyl, and cyano.

In the formula II.a, the radical W is preferably a $C_{1-10}$-alkylene group, such as a $C_{2-8}$-alkylene group. Another preferred meaning of the group W is a bridge having from 1 to 20 carbon atoms, which may have interruption by up to 10 non-adjacent oxygen atoms. These are then low-molecular-weight polyoxyalkylene groups which contain repeat units which derive from ethylene oxide, from propylene oxide, from tetrahydrofuran, or from any desired combinations of these. The group W may moreover be a polyoxyalkylene group having more than 21 carbon atoms.

Preference is given to compounds of the formula I.a where $R^{23}$, $R^{24}$, $R^{25}$, $R^{26}$, $R^{27}$, $R^{28}$, and $R^{29}$ are hydrogen. Preference is also given to compounds of the formula I.a where $R^{25}$, $R^{26}$, and $R^{27}$ are hydrogen and $R^{23}$, $R^{24}$, $R^{28}$, and $R^{29}$ are $C_{1-4}$-alkyl, particularly preferably methyl. Preference is also given to compounds of the formula I.a where $R^{23}$ and $R^{28}$ are $C_{1-4}$-alkyl, particularly preferably methyl, and $R^{24}$, $R^{25}$, $R^{26}$, $R^{27}$, and $R^{29}$ are hydrogen. Each of the phenyl radicals in positions 2 and 6 of the phosphacyclohexane ring of the compounds of the formula I.a preferably has an alkyl radical in position 2 or two alkyl radicals in positions 2 and 4. The radical R in the compounds of the formula I.a (and also I.b to I.f and II.a) is preferably $C_{1-14}$-alkyl, such as propyl, n-butyl, sec-butyl, isobutyl, n-octyl, 2-ethylhexyl, dodecyl, or else cyclohexyl, methoxyethoxyethyl, or a polymer radical, such as a polyethylene radical or polybutadiene radical.

In the compounds of the formula I.b, the radicals $R^{23}$, $R^{24}$, $R^{25}$, $R^{26}$, $R^{28}$, $R^{29}$, $R^{30}$, and $R^{31}$ have preferably been selected from hydrogen and $C_{1-4}$-alkyl, hydrogen being particularly preferred.

In the compounds of the formula I.c, the radicals $R^{32}$, $R^{33}$, and $R^{34}$ are preferably tert-butyl.

The compound of the formula I.e is particularly preferably a 1,2,7,8-dibenzo-3,4,5,6-tetrahydro-9-phosphaanthracene molecule.

In the compounds of the formula I.f, the radicals $R^{23}$, $R^{24}$, $R^{25}$, $R^{26}$, $R^{28}$, and $R^{29}$ have particularly preferably been selected from hydrogen and $C_1$–$C_4$-alkyl, methyl being particularly preferred. The phenyl radicals of the phosphacyclohexanones of the formula I.f preferably have a substituent other than hydrogen in position 2, two substituents other than hydrogen in positions 2 and 4, or three substituents other than hydrogen in positions 2, 4, and 6.

Particular preference is given to compounds of the formula I.g where $R^{35}$, $R^{36}$, $R^{37}$, and $R^{38}$ are $C_{1-4}$-alkyl, in particular methyl.

In relation to preferred substituents for the compounds of the formula II.a, the description given above for compounds of the formula I.a applies. The bridging group W is preferably a $C_{1-10}$-alkylene group, such as a $C_2$–$C_8$-alkylene group.

Catalyst systems suitable for the process of the invention may comprise complexers other than the abovementioned phosphorus-containing ligands. Some examples of these are carbonyl groups, hydride groups, nitrogen-containing ligands, such as amines, amides, or nitrogen heterocycles, sulfates, nitrates, and carboxylates. Rhodium catalysts suitable for use in the process of the invention and having no phosphine ligands are also termed "naked" rhodium catalysts below.

Examples of "naked" rhodium catalysts and their use in the hydroformylation of olefins are found, for example, in Chem. Ber. 102, 2238 (1969), Tetrahedron Lett. 29, 3261 (1968) and Hydrocarbon Process. 85–86 (1975). There are also patent applications and patents relating to this sector, for example U.S. Pat. No. 4,400,547, DE-A-33 38 340, DE-A-26 04 545 and WO 82/03856.

The rhodium catalysts described in DE-A-198 01 437 are also particularly suitable for the inventive use. These are rhodium catalysts which, as ligand, bear derivatized, essentially non-water-soluble polyamines which are capable of complex formation and have an average molecular weight >1000 dalton and having at least 10 nitrogen atoms.

The ligands are particularly derivatized polyamines with an average molecular weight above 1000 dalton. In the most preferred embodiment the polyamine is a polyethyleneimine substantively composed of units of the formula (IV) below.

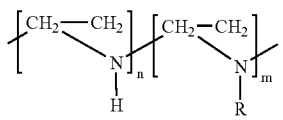

IV

In formula IV m+n is at least 10 and the ratio m/m+n is from 0.01 to 1, and R is identical or different alkyl, cycloalkyl, aryl, aralkyl, alkylcarbonyl radicals having up to 30 carbon atoms, or is hydroxyalkyl(poly)oxyalkylene radicals having up to 500 alkyleneoxy units.

The rhodium complexes disclosed in DE-A-198 01 437 are an integral constituent of the present invention and are incorporated into the present application by way of reference.

The amount used of the rhodium catalysts used according to the invention is generally in the range from about 1 to 150 ppm, preferably from 1 to 100 ppm. The reaction temperature is generally in the range from room temperature to 200° C., preferably from 50 to 180° C., in particular from 80 to 150° C. The reaction may be carried out at an elevated pressure from about 10 to 1000 bar, preferably from 20 to 650 bar, in particular from 80 to 350 bar.

The molar ratio $H_2$:CO is generally from about 1:5 to about 5:1, preferably from 1:2 to 2:1.

The aldehydes or aldehyde/alcohol mixtures produced during the hydroformylation may, if desired, be isolated and, where appropriate, purified by methods known to the skilled worker prior to the hydrogenation process. It is preferable for the hydroformylation catalyst to be removed from the reaction mixture prior to the hydrogenation process. It can generally be reused for the hydroformylation process, where appropriate after treatment. For the hydrogenation process the reaction mixtures obtained during the hydroformylation are reacted with hydrogen in the presence of a hydrogenation catalyst.

Suitable hydrogenation catalysts are generally transition metals, e.g. Cu, Cr, Mo, W, Fe, Rh, Co, Ni, Pd, Pt, Ru, etc., or mixtures of these, and to increase activity and stability they may be applied to supports, e.g. activated carbon, aluminum oxide, silicon dioxide, kieselghur, etc. To increase catalytic activity it is also possible to use Fe, Co, and preferably Ni in the form of Raney catalysts as a spongiform metal with very high surface area. Preference is given to the use of heterogeneous catalysts which have become established in industry, for example active compositions on supports or unsupported catalysts, used, for example, by the up flow or down flow method, or in suspension. The pressure is preferably in the range from about 5 to 350 bar. It is preferable to use a slight molar excess of hydrogen.

Use may also be made of other processes for the reduction of the aldehydes to give the alcohols. Examples of these are reduction using complex hydrides, e.g. $LiAlH_4$ or $NaBH_4$, Bouveault-Blanc reduction using sodium in ethanol, and also other known processes.

The alcohol mixtures of the invention are obtainable advantageously by the inventive process described. If a $C_{12}$–$C_{14}$ monoolefin mixture accessible on a large industrial scale is hydroformylated by the inventive process in the presence of a rhodium catalyst and then hydrogenated, the result is a $C_{13}$–$C_{15}$ alcohol mixture whose isomer distribution differs from that of, for example, a $C_{13}$–$C_{15}$ alcohol mixture which was prepared by cobalt-catalyzed hydroformylation. After processing, the alcohol mixtures of the invention give surface-active compounds with advantageous properties. Examples of these are good biodegradability, low foaming, and a gel region which covers only a small range of concentrations.

The invention also provides a process for preparing functionalized alcohol mixtures, where an alcohol mixture, as described above, is subjected to alkoxylation, glycosidation, sulfation, phosphation, alkoxylation followed by sulfation, or alkoxylation followed by phosphation.

The invention therefore provides a process for preparing functionalized alcohol mixtures, where a) a monoolefin mixture is prepared, substantively comprising olefins having 12 to 14 carbon atoms and having linear α-olefins and from 5 to 20% by weight of olefins other than these, and b) the monoolefin mixture is hydroformylated by reaction with carbon monooxide and hydrogen in the presence of a rhodium catalyst, and is then hydrogenated, and c) the alcohol mixture from step b) is subjected to alkoxylation, glycosidation, sulfation, phosphation, alkoxylation followed by sulfation, or alkoxylation followed by phosphation.

The alcohol mixtures are alkoxylated by reaction with at least one alkylene oxide. Preference is given to alkylene oxides selected from the group consisting of compounds of the formula II

(II)

where $R^b$ is hydrogen or straight-chain or branched $C_1$–$C_{16}$-alkyl, or a mixture of these.

$R^b$ in formula II is preferably straight-chain or branched $C_1$–$C_8$-alkyl, in particular $C_1$–$C_4$-alkyl.

Preference is given to alkylene oxides selected from the group consisting of ethylene oxide, propylene oxide, butylene oxide, pentylene oxide and mixtures of these.

The reaction of the alcohol mixtures with the alkylene oxide(s) takes place by conventional processes known to the skilled worker and in apparatuses conventional for this purpose.

The average chain length of the polyether chains of the alcohol mixtures functionalized in this way may be determined via the molar quantity ratio of alcohol to alkylene oxide. Preference is given to the preparation of alkoxylated alcohol mixtures having from about 1 to 200 alkylene oxide units, preferably from about 1 to 100 alkylene oxide units, in particular from 1 to 50 alkylene oxide units.

If desired, the alcohol mixtures may be reacted with just one alkylene oxide or with two or more different alkylene oxides. When the alcohol mixtures are reacted with a mixture made from two or more alkylene oxides, the alkylene oxide units are essentially randomly distributed in the resultant alkoxylates. If the alkylene oxides are used separately one after the other, the resultant alkoxylates contain polymerized blocks of the alkylene oxide units as determined by the sequence of addition.

The alkoxylation may be catalyzed by strong bases, such as alkali metal hydroxides and alkaline-earth metal hydroxides, Brönsted acids or Lewis acids, such as $AlCl_3$, $BF_3$ etc.

The alkoxylation preferably takes place at from about 80 to 250° C., preferably from about 100 to 220° C. The pressure is preferably from atmospheric pressure to 600 bar. If desired, the alkylene oxide may comprise a mixture of, for example, from 5 to 60% of an inert gas.

The functionalized alcohol mixtures obtained by alkoxylation show very good surface activity and may be used advantageously as nonionic surfactants in a variety of application sectors.

The alcohol alkoxylates prepared to the invention may, if desired, be converted into end-group-alkylated surfactants by reaction with alkylating reagents, such as methyl chloride, dimethyl sulfate, diethyl sulfate, butyl chloride, or isobutene.

The glycosidation of the alcohol mixtures takes place by single, double or multiple reaction of the novel alcohol mixtures with mono-, di- or polysaccharides. The reaction takes place by conventional processes known to the skilled worker. These include firstly acid-catalyzed reaction with elimination of water. Examples of suitable acids are mineral acids, such as HCl and $H_2SO_4$. This generally gives oligosaccharides with a random chain length distribution. The average degree of oligomerization is preferably from 1 to 3 saccharide radicals. In another suitable process the saccharide may firstly be acetalized by reaction with a low-molecular-weight $C_1$–$C_8$ alkanol, e.g. ethanol, propanol or butanol. The acetalization preferably takes place with acid catalysis. The resultant glycoside with the low-molecular-weight alcohol may then be reacted with a novel alcohol mixture to give the corresponding glycosides. Aqueous saccharide solutions are generally also suitable for this reaction. In another suitable process the saccharide may firstly be converted into the corresponding O-acetylhalosaccharide by reaction with a hydrogen halide and then undergo glycosidation with a novel alcohol mixture in the presence of acid-binding compounds.

It is preferable to use monosaccharides for the glycosidation. Use is in particular made of hexoses, such as glucose, fructose, galactose, mannose, etc., and pentoses, such as arabinose, xylose, ribose, etc. Particular preference is given to the use of glucose. The saccharides may be used individually or in the form of mixtures. When saccharide mixtures are used the resultant glycosides generally have randomly distributed sugar radicals. In the case of multiple saccharide addition reactions onto an alcoholic hydroxyl group the result is polyglycosides of the novel alcohol mixtures. It is also possible to use two or more saccharides one after the other or as a mixture for polyglycosidation, so that the resultant functionalized alcohol mixtures contain the saccharides either in the form of blocks or randomly distributed. Depending on the reaction conditions, in particular the reaction temperature, furanose structures or pyranose structures may result.

Suitable processes and reaction conditions for glycosidation are described, for example, in Ullmanns Encyclopedia of Industrial Chemistry, 5th ed., Vol. A25 (1994), pp. 792–793 and in the literature references found there.

The functionalized alcohol mixtures obtained by glycosidation show very good surface activity and may be used advantageously as nonionic surfactants in a variety of application sectors.

The sulfation or phosphation of the alkoxylated alcohol mixtures or alcohol mixtures described above takes place by reaction with sulfuric acid or with sulfuric acid derivatives to give acid alkyl sulfates or alkyl ether sulfates, or by reaction with phosphoric acid or with phosphoric acid derivatives to give acid alkyl phosphates or alkyl ether phosphates.

Suitable processes for the sulfation of alcohols are those which are conventional and known to the skilled worker, as described, for example, in U.S. Pat. No. 3,462,525, U.S. Pat. No. 3,420,875 or U.S. Pat. No. 3,524,864, the entire scope of which is incorporated herein by way of reference. Suitable processes for the sulfation are also described in Ullmanns Encyclopedia of Industrial Chemistry, 5th ed. Vol A25 (1994), pp. 779–783 and in the literature references found there.

If sulfuric acid is used for the sulfation of the novel alcohol mixtures, its strength is preferably from 75 to 100% by weight, in particular from 85 to 98% by weight. Sulfuric acid of this type is available under the names concentrated sulfuric acid and monohydrate.

If desired, a solvent or diluent may be used for the sulfation with sulfuric acid. Examples of suitable solvents are those which form an azeotropic mixture with water, for example toluene.

In one suitable embodiment for preparing sulfated alcohol mixtures, the alcohol mixture is charged to a reaction vessel and the sulfating agent is added with continuous mixing. To achieve very complete esterification of the alcohol mixture, the molar quantity ratio of alkanol to sulfating agent is preferably from about 1:1 to 1:1.5, in particular from 1:1 to 1:1.2. If desired, the sulfating agent may also be used in substoichiometric amounts, e.g. in sulfating alkoxylated alcohol mixtures, if the intention is to prepare mixtures of nonionic and anionic surface-active compounds. The sulfation preferably takes place at from room temperature to 80° C., in particular at from 40 to 75° C.

Examples of other suitable sulfating agents are sulfur trioxide, sulfur trioxide complexes, solutions of sulfur trioxide in sulfuric acid (oleum), chlorosulfonic acid, sulfuryl chloride, amidosulfonic acid, etc. If sulfur trioxide is used as sulfating agent the reaction may advantageously be carried out in a falling-film evaporator, preferably in countercurrent. The reaction here may take place batchwise or continuously.

The work-up of the reaction mixtures produced by the sulfation takes place by conventional processes known to the skilled worker. These include neutralization, separation of any solvents used, etc.

The phosphation of the alkoxylated alcohol mixtures and alcohol mixtures described above generally takes place in a manner analogous to the sulfation.

Suitable processes for the phosphation of alcohols are those which are conventional and known to the skilled worker, as described, for example, in Synthesis 1985, pp. 449–488, the entire scope of which is incorporated herein by way of reference.

Examples of suitable phosphating agents are phosphoric acid, polyphosphoric acid, phosphorus pentoxide, $POCl_3$, etc. If $POCl_3$ is used the remaining acid chloride functions are hydrolyzed after the esterification.

The functionalized alcohol mixtures obtained by sulfation or phosphation, and salts of these, show very good surface activity and may be used advantageously as anionic surfactants in a wide variety of application sectors.

The present invention further relates to the functionalized alcohol mixtures obtainable by the process described above, and salts of these.

The present invention further relates to the use of the functionalized alcohol mixtures as described above as surfactants, or as or in dispersants, paper auxiliaries, textile auxiliaries, leather auxiliaries, or detergents, corrosion inhibitors, auxiliaries for dispersions, or encrustation inhibitors, or else in products for the metalworking industry, in products for electroplating processes, in surface-coatings, in printing inks, in pigment preparations, in crop-protection formulations, in water treatment, or in the plastics processing industry.

The alkoxylates, in particular, exhibit advantageous properties. When $C_{13}$–$C_{15}$ alcohol alkoxylates obtainable from the alcohols of the invention are tested for biodegradability (to OECD 301 B) they are markedly faster than comparable alkoxylates in achieving the pass level of 60% $CO_2$ formation. Since the surfactants of the invention are used especially in applications which affect aqueous wastes, e.g. detergents and hard-surface cleaners, this is a decisive advantage.

The gelling behavior of these inventive $C_{13}$–$C_{15}$ alcohol alkoxylates is also surprising. The skilled worker knows that the gel region here depends on the linearity of the alcohol. For the purposes of the current application, this linearity is defined as the total of alcohols which are unbranched or have a low degree of branching, including linear alcohols and those having 2-methyl or 2-ethyl structure. If the linearity is relatively high, the resultant surfactants have well-developed gelling behavior, i.e. broader gel phases on dilution with water. However, Brookfield viscosity measurements at various concentrations of the inventive surfactants in water reveals either complete absence of a gel region or a markedly diminished gel region.

This is associated with advantages especially in solid detergents and solid cleaning compositions, irrespective of whether these detergents or cleaning compositions are in powder, pellet, extrudate, or tablet form. When these solid products are dissolved in water there is a marked diminution of the gel phase which has to be traversed, and the dissolution process therefore proceeds more rapidly, the result being that there is a longer time for the full surfactant concentration to have an advantageous effect upon the product to be cleaned. Cleaning power is therefore increased.

Another surprising phenomenon is the low foaming of the surfactants based on the $C_{13}$–$C_{15}$ alcohols of the invention. It is generally true that surfactants based on linear alcohols give heavier foaming than surfactants based on branched alcohols. The result found using the surfactants of the invention is contradictory to the theory.

The lower foaming is another advantage in many detergents and cleaning compositions. For example, it is possible to use smaller amounts of foam suppressants, e.g. silicones or alcohol propoxylates. This is especially important with solid or liquid detergents. Secondly, these surfactants can be used in sectors where the cleaning process tends to cause heavy foaming, for example in spray-cleaning processes or in high-pressure cleaning systems.

In detergents, the surfactants of the invention, preferably nonionic $C_{13}$–$C_{15}$ alcohol alkoxylates, may be combined with the conventional additives known to the skilled worker in amounts of from 0.1 to 40% by weight, preferably from 0.5 to 30% by weight, most preferably from 1 to 20% by weight. Examples of suitable additives are:

builders and cobuilders, such as polyphosphates, zeolites, polycarboxylates, phosphonates, citrates, complex-formers;

ionic surfactants, such as alkylbenzenesulfonates, α-olefinsulfonates, and alcohol sulfates/alcohol ether sulfates, and also the inventive $C_{13}$–$C_{15}$ alcohol sulfates/alcohol ether sulfates, and sulfosuccinates;

nonionic surfactants, such as alkylaminoalkoxylates and alkylpolyglucosides, amphoteric surfactants, e.g. alkylamine oxides and betaines, and also the inventive $C_{13}$–$C_{15}$ alkylpolyglucosides;

optical brighteners;

color-transfer inhibitors, e.g. polyvinylpyrrolidone;

extenders, e.g. sodium sulfate, magnesium sulfate;

soil-release agents, e.g. polyethers/polyesters, carboxymethylcellulose;

encrustation inhibitors, e.g. polyacrylates, copolymers made from acrylic acid and maleic acid;

bleaching systems composed of bleaches such as perborate or percarbonate plus bleaching activators, such as tetraacetylethylenediamine plus bleach stabilizers;

fragrance;

foam suppressants, e.g. silicone oils, alcohol propoxylates (especially in liquid detergents);

enzymes, e.g. amylases, lipases, proteases or carboxylases;

alkali donors, e.g. pentasodium metasilicate or sodium carbonate.

Other constituents known to the skilled worker may likewise be present.

The pulverulent detergents in their conventional form have an average bulk density of about 450 g/l. Compact or ultracompact detergents have a bulk density >600 g/l. The importance of these is constantly increasing.

Liquid detergents may also comprise solvents, e.g. ethanol, isopropanol, propylene 1,2-glycol, or butylene glycol.

Gel-type detergents also comprise thickeners, e.g. polysaccharides and weakly crosslinked polycarboxylates (e.g. the Carbopol® grades from BF Goodrich).

Detergents in tablet form require other additives. Examples of these are tabletting auxiliaries, e.g. polyethylene glycols with molar masses >1000 g/mol, or polymer dispersions. Tablet disintegrants, e.g. cellulose derivatives, crosslinked polyvinylpyrrolidone, crosslinked polyacrylates, or combinations of acids, e.g. citric acid, with sodium carbonate.

In cleaners for hard surfaces, e.g. acidic cleaners, alkaline cleaners, neutral cleaners, machine dishwashing, metal degreasing, glass cleaners, and floor cleaners, to name just a few, the nonionic $C_{13}$–$C_{15}$ alcohol alkoxylates of the invention are combined with the existing additives listed below in amounts of from 0.01 to 40% by weight, preferably from 0.1 to 20% by weight:

ionic surfactants, such as the inventive $C_{13}$–$C_{15}$ alcohol sulfates/alcohol ether sulfates, alkylbenzenesulfonates, α-olefinsulfonates, and other alcohol sulfates/alcohol ether sulfates, and sulfosuccinates;

nonionic surfactants, such as alkylaminoalkoxylates and alkylpolyglucosides, and also the inventive $C_{13}$–$C_{15}$-alkylpolyglucosides;

amphoteric surfactants, e.g. alkylamine oxides and betaines;

builders, e.g. polyphosphates, polycarboxylates, phosphonates, complex-formers;

dispersants, e.g. naphthalenesulfonic acid condensates, polycarboxylates;

pH-regulating compounds, e.g. alkalis, such as NaOH or KOH, or pentasodium metasilicate, or acids, such as hydrochloric acid, phosphoric acid, amidosulfuric acid, citric acid;

enzymes, e.g. amylases, lipases, proteases or carboxylases;

fragrance;

dyes;

biocides, e.g. isothiazolinones, 2-bromo-2-nitro-1,3-propanediol;

bleaching systems composed of bleaches such as perborate or percarbonate plus bleaching activators, such as tetraacetylethylenediamine plus bleach stabilizers;

solubilizers, e.g. cumenesulfonates, toluenesulfonates, short-chain fatty acids, alkyl/aryl phosphates;

solvents, e.g. short-chain alkyl oligoglycols, alcohols, such as ethanol or propanol, aromatic solvents, such as toluene or xylene, N-alkylpyrrolidones, alkylene carbonates;

thickeners, e.g. polysaccharides and weakly crosslinked polycarboxylates (e.g. the Carbopol® grades from BF Goodrich).

These hard-surface cleaners are usually, but not always, aqueous and they take the form of microemulsions, emulsions or solutions.

If they are in solid form, use may also be made of extenders, as described above.

Cleaners in tablet form require other additives. Examples of these are tabletting auxiliaries, e.g. polyethylene glycols with molar masses >1000 g/mol, or polymer dispersions. Tablet disintegrants, e.g. cellulose derivatives, crosslinked polyvinylpyrrolidone, crosslinked polyacrylates, or combinations of acids, e.g. citric acid, with sodium carbonate.

The surfactants may also be used advantageously for a wide variety of other processes in the chemical industry, for example generally in the metal working industry, for example in cooling lubricants,
quenching oils,
hydraulic oil emulsions,
polishing pastes,
mold-release agents,
drawing oils,
pickling agents,
metal cleaners,
metal drying agents.

The surfactants here may specifically be used advantageously in those processes where high thermal stability is important.

The surfactants may also be used in the production and processing of textiles. There is extraordinarily wide use of surfactants in the production and processing of textiles, covering primarily the sectors of fiber pretreatments,
production of Reyon fibers,
spinning preparations and textile lubricants,
dyeing assistants,
finishing agents,
water repellents,
printing assistants,
antistats,
agents for flocking or coating processes.

The surfactants may also be used in the leather industry, in papermaking, in the printing industry, in the electroplating industry, and in the photographic industry. Important application sectors here are surface-coatings, pigments, and printing inks. The surfactants are used in these application sectors either in aqueous systems or in non-aqueous systems. In non-aqueous systems, they serve especially as dispersants, antisettling agents, or leveling agents. In addition, surfactants permit the preparation of what are known as high-solids systems, in which they serve not only to stabilize the polymer-dispersion-based binders prepared by emulsion polymerization or emulsion polycondensation, but also as dispersants for the organic or inorganic pigments frequently used. Besides this, they improve the adhesion properties of these paints.

The surfactants may also be used in water treatment, for example in waste-water purification.

The surfactants may also be used in crop-protection formulations.

The compounds may also be used as surfactants or emulsifiers in the industrial sectors of plastics production and plastics processing. The principle application sectors in plastics production and plastics processing are preparation of polymer dispersions,
preparation of bead polymers,
preparation of foams,
use of surface-active mold-release agents,
preparation of microcapsules,
improvement of adhesion between fillers and plastics,
additives for polymer dispersions to achieve particular effects, such as foamability, filler-compatibility, or wetting power,
emulsifiers for non-aqueous systems,
coloration of plastics,
giving antistatic properties to plastics,
adhesives.

The process of the invention will now be described in greater detail in the examples below. Biodegradability here was tested to the OECD guidelines, and in this specifically OECD 301 B. Foaming was tested to DIN 53902 Sheet 1 at a concentration of 2 g/l. The value given corresponds to the V2 value in the DIN standard. Viscosity was measured using a Brookfield viscometer of LVT type. The surfactants were diluted in advance with water as appropriate, and care was taken that the solution was free from bubbles. If the viscosity exceeds 10000 mPas a gel is assumed to be present.

EXAMPLES

Example 1

Preparation of a $C_{13}$–$C_{15}$ Alcohol Mixture by Rhodium-Catalyzed Hydroformylation of a $C_{12}$–$C_{14}$ Olefin Mixture and Subsequent Hydrogenation of the Mixture An industrial $C_{12}$–$C_{14}$ α-olefin mixture with the composition given in Table I was hydroformylated in a continuously operated hydroformylation plant. For this, olefin mixture and a catalyst solution were fed into a cascade of two stirred autoclave reactors each with 1.6 liter liquid capacity, where they were reacted at 280 bar at a rhodium concentration of about 20 mg/kg of reactor contents at 115° C. (first reactor) and 135° C. (second reactor) with synthesis gas whose mixing ratio of CO/$H_2$ was 1:1. The catalyst comprised a polyethyleneimine whose preparation was based on Example 4 of DE-A 198 01 437 and whose molecular weight Mw was 460 000, and which had been amidated with about 60 mol % of lauric acid, based on the amine groups present, and which was therefore capable of homogeneous solution in the catalyst phase and in the reaction zone. The molar ratio of nitrogen from the polymeric ligands to rhodium was about 100. The pressure on the discharge from the reactors was released and the remaining gas separated off. The liquid phase was passed into an evaporator where a stream of overhead product was separated off at 170° C. and a pressure of about 10 mbar.

Conversion, based on total olefin, was 98.3%, selectivity (aldehyde+alcohol) was 98%, paraffin selectivity was 1%, and selectivity in giving higher-boiling aldehyde condensation products was 1%. The stream of bottom product comprised the rhodium catalyst and amidated polyethyleneimine and substantively the high-boiling condensation products of the aldehydes, and was returned to the reaction zone as catalyst solution. The stream of overhead products from the evaporator was hydrogenated in a continuously operated hydrogenation plant without any further prior work-up. For this, the stream was hydrogenated with addition of 10% by weight of water at 170° C. and a hydrogen pressure of 280 bar by the downflow method in a tubular reactor provided with a heterogeneous catalyst (supported Cu catalyst). Once pressure had been released and the hydrogen had been separated off, the crude discharge was subjected to fractional distillation. The hydrocarbons were discarded. All of the $C_{13}$–$C_{15}$ alcohol fractions were combined and their composition was determined (Table II) by gas chromatography with an internal standard and correction factors.

TABLE I

Composition of $C_{12}$–$C_{14}$ α-olefin mixture used:

| | % by weight |
|---|---|
| $C_{12}$ olefins | 67 |
| $C_{14}$ olefins | 33 |
| α-olefins | 88.6 |

TABLE I-continued

Composition of $C_{12}$–$C_{14}$ α-olefin mixture used:

| | % by weight |
|---|---|
| non-terminal linear olefins | 2.5 |
| vinylidene-branched olefins + other olefin isomers | 8.9 |

TABLE II

Composition of $C_{13}$–$C_{15}$ alcohol mixture after hydrogenation and distillation:

| | % by weight |
|---|---|
| unbranched alcohols | 50 |
| 2-methyl-branched alcohols | 34 |
| 2-ethyl-branched alcohols | 4 |
| higher branched alcohols | 12 |

Example 2 (Comparative Example)

$C_{13}$–$C_{15}$-Alcohol Via Cobalt-Catalyzed Hydroformylation of a $C_{12}$–$C_{14}$ Olefin Mixture and Subsequent Hydrogenation The $C_{12}$–$C_{14}$ α-olefin mixture from Example 1 with the composition shown in Table I was hydroformylated in the manner indicated in Example 1. Unlike Example 1, instead of the rhodium catalyst and the polyethyleneimine ligand, the hydroformylation catalyst used was dicobaltoctacarbonyl without any other ligand, the amount being 2 g of cobalt based on 1000 g of reactor contents. In order that the olefin conversion obtained was from 98 to 99%, as in Example 1, using the same olefin feed, a reactor temperature of 140° C. was required in both reactors. The (aldehyde+alcohol) selectivity was 94%, the paraffin selectivity was 3%, and the selectivity to give higher-boiling aldehyde condensation products was 3%. Once the pressure in the reactors had been released, the discharge was treated with aqueous acetic acid solution while introducing atmospheric oxygen, until the cobalt carbonyl had been oxidized to give cobalt acetate. The aqueous, cobalt-containing phase was separated off in a phase separator, and the organic phase, as in Example 1, hydrogenated and distilled. Table III gives the composition of the $C_{13}$–$C_{15}$ alcohol mixture.

TABLE III

Composition of $C_{13}$–$C_{15}$ alcohol mixture after hydrogenation and distillation

| | % by weight |
|---|---|
| unbranched alcohols | 58 |
| 1-methyl-branched alcohols | 17 |
| 1-ethyl-branched alcohols | 6 |
| other alcohols | 19 |

Examples 3–6

Preparation of Oxo Alcohol Ethoxylates

Example 3

Preparation of a $C_{13}$–$C_{15}$ Oxo Alcohol Ethoxylate Using 7 Mol of Ethylene Oxide 416 g of $C_{13}$–$C_{15}$ fatty alcohol (from Example 1) are charged, with 1.5 g of NaOH, to a dry 2 l autoclave. The contents of the autoclave are heated to 150° C., and then 616 g of ethylene oxide are introduced into the autoclave under pressure. Once the entire amount of ethylene oxide is in the autoclave, the autoclave is held at 150° C. for 30 minutes. Cooling is followed by neutralization of the catalyst with acetic acid.

The resultant surfactant has a cloud point of 77° C., measured at 1% strength in water in a 10% strength butyl diglycol solution to DIN 53917. The surface tension is 27.9 mN/m, measured to DIN 53914, at a concentration of 1 g/l.

Example 4

Preparation of a $C_{13}$–$C_{15}$ Oxo Alcohol Ethoxylate Using 11 Mol of Ethylene Oxide 312 g of $C_{13}$–$C_{15}$ fatty alcohol (from Example 1) are charged, with 1.5 g of NaOH, to a dry 2 l autoclave. The contents of the autoclave are heated to 150° C., and then 726 g of ethylene oxide are introduced into the autoclave under pressure. Once the entire amount of ethylene oxide is in the autoclave, the autoclave is held at 150° C. for 30 minutes. Cooling is followed by neutralization of the catalyst with acetic acid.

The resultant surfactant has a cloud point of 85.8° C., measured at 1% strength in water to DIN 53917. The surface tension is 32.4 mN/m, measured to DIN 53914, at a concentration of 1 g/l.

Example 5 (Comparative Example)

Preparation of a $C_{13}$–$C_{15}$ Oxo Alcohol Ethoxylate Using 7 Mol of Ethylene Oxide 416 g of $C_{13}$–$C_{15}$ fatty alcohol (from Example 2) are charged, with 1.5 g of NaOH, to a dry 2 l autoclave. The contents of the autoclave are heated to 150° C., and then 616 g of ethylene oxide are introduced into the autoclave under pressure. Once the entire amount of ethylene oxide is in the autoclave, the autoclave is held at 150° C. for 30 minutes. Cooling is followed by neutralization of the catalyst with acetic acid.

The resultant surfactant has a cloud point of 76.7° C., measured at 1% in water strength in a 10% strength butyl diglycol solution to DIN 53917. The surface tension is 28 mN/m, measured to DIN 53914, at a concentration of 1 g/l.

Example 6 (Comparative Example)

Preparation of a $C_{13}$–$C_{15}$ Oxo Alcohol Ethoxylate Using 11 Mol of Ethylene Oxide 312 g of $C_{13}$–$C_{15}$ fatty alcohol (from Example 2) are charged, with 1.5 g of NaOH, to a dry 2 l autoclave. The contents of the autoclave are heated to 150° C., and then 726 g of ethylene oxide are introduced into the autoclave under pressure. Once the entire amount of ethylene oxide is in the autoclave, the autoclave is held at 150° C. for 30 minutes. Cooling is followed by neutralization of the catalyst with acetic acid.

The resultant surfactant has a cloud point of 85.5° C., measured at 1% strength in water to DIN 53917. The surface tension is 31.5 mN/m, measured to DIN 53914, at a concentration of 1 g/l.

Biodegradability, foaming, and viscosity as a function of water content were determined for each of the oxo alcohol ethoxylates obtained in Examples 3–6. The results are given in Tables IV–VI below. FIGS. 1 and 2 show viscosity as a function of water content.

TABLE IV

Results using OECD 301 A/B combination test

|  | OECD 301 B - time in days for $CO_2$ fall-off from 10 to 60% |
|---|---|
| Example 3 | 7.5 |
| Example 4 | 8 |
| Example 5 (comparison) | 9 |
| Example 6 (comparison) | 8.5 |

TABLE V

Mechanical foaming to DIN 53901 Bl. 1(concentration 2 g/l)

|  | Foam volume in ml |
|---|---|
| Example 3 | 190 |
| Example 4 | 270 |
| Example 5 (comparison) | 250 |
| Example 6 (comparison) | 400 |

TABLE VI

Viscosity in mPas (Brookfield at 23° C., D = 60 l/s)

| Water content in % | Example 3 | Example 4 | Example 5 (comparison) | Example 6 (comparison) |
|---|---|---|---|---|
| 0 | 900 | Paste | 500 | Paste |
| 10 | 120 | 160 | 110 | 110 |
| 20 | 8700 | 320 | Gel | 200 |
| 30 | 5300 | 780 | Gel | 600 |
| 40 | 3100 | Gel | 3900 | Gel |
| 50 | 1400 | Gel | 1900 | Gel |
| 60 | 4500 | 1000 | 900 | Gel |
| 70 | 1800 | 330 | 1000 | 160 |
| 80 | 230 | 10 | 850 | 10 |
| 90 | 10 | 5 | 230 | 5 |

Example 7

Preparation of a $C_{13}$–$C_{15}$ Oxo Alcohol Ethoxylate Using 3 Mol of Ethylene Oxide 624 g of the alcohol prepared in Example 1 are charged, with 1.5 g of NaOH, to a dry 2 l autoclave. The contents of the autoclave are heated to 150° C., and then 396 g of ethylene oxide are introduced into the autoclave under pressure. Once the entire amount of ethylene oxide is in the autoclave, the autoclave is held at 150° C. for 30 minutes. Cooling is followed by neutralization of the catalyst with sulfuric acid.

The resultant surfactant has a cloud point of 46.3° C., measured at 1% strength in a 10% strength butyl diglycol solution to DIN 53917. The surface tension is 28.6 mN/m, measured to DIN 53914, at a concentration of 1 g/l.

Example 8

Preparation of an Alkyl Phosphate 312 g of the alcohol prepared in Example 1 are heated to 60° C. under nitrogen in a stirred vessel and slowly mixed with 125 g of polyphosphoric acid. During this process the temperature should not exceed 65° C. Toward the end of the addition, the temperature is increased to 70° C. and the mixture is stirred at this temperature for one hour.

Surface tension measured to DIN 53914 is 37.1 mN/m at a concentration of 1 g/l.

Example 9

Preparation of an Alkyl Ether Phosphate 510 g of the $C_{13}$–$C_{15}$ alcohol ethoxylate prepared in Example 7 are heated to 60° C. under nitrogen in a stirred vessel and slowly mixed with 125 g of polyphosphoric acid. During this process the temperature should not exceed 65° C. Toward the end of the addition, the temperature is increased to 70° C. and the mixture is stirred at this temperature for one hour.

Surface tension measured to DIN 53914 is 36.1 mN/m at a concentration of 1 g/l.

Example 10

Preparation of an Alkyl Sulfate 208 g of the alcohol prepared in Example 1 are slowly mixed with 132 g of chlorosulfuric acid under nitrogen in a stirred vessel. The temperature should not exceed 30° C. during this process. This mixture is added to a solution of 45 g of NaOH in 710 ml of water.

Surface tension measured to DIN 53914 is 31.8 mN/m at a concentration of 1 g/l.

Example 11

Preparation of an Alkyl Ether Sulfate 510 g of the $C_{13}$–$C_{15}$ alcohol ethoxylate prepared in Example 7 are slowly mixed with 198 g of chlorosulfuric acid under nitrogen in a stirred vessel. The temperature should not exceed 30° C. during this process. The mixture is added to a solution of 67 g of NaOH in 1500 ml of water.

Surface tension measured to DIN 53914 is 34.2 mN/m at a concentration of 1 g/l.

Example 12

Preparation of a $C_{13}$–$C_{15}$ Alcohol Alkoxylate 212 of the alcohol prepared in Example 1 are charged, with 0.2 g of KOH, to a dry 2 l autoclave. The contents of the autoclave are heated to 130–140° C., and 290 g of propylene oxide are introduced into the autoclave under pressure. Once the entire amount of propylene oxide is in the autoclave, the autoclave is held at 130–140° C. for 120 minutes. 132 g of ethylene oxide are then introduced into the autoclave under pressure at 110–120° C., and the autoclave is held for 60 minutes at this temperature. Cooling is followed by neutralization of the catalyst with acetic acid.

The resultant surfactant has a cloud point of 44° C., measured at 1% strength in a 10% strength butyl diglycol solution to DIN 53917. The surface tension is 31.2 mN/m, measured to DIN 53914, at a concentration of 1 g/l.

Example 13

Preparation of a $C_{13}$–$C_{15}$ Alcohol Alkoxylate 318 g of the alcohol prepared in Example 1 are charged, with 0.3 g of KOH, to a dry 2 l autoclave. The contents of the autoclave are heated to 110–120° C., and 660 g of ethylene oxide are introduced into the autoclave under pressure. Once the entire amount of propylene oxide is in the autoclave, the autoclave is held at 110–120° C. for 60 minutes. 200 g of butylene oxide are then introduced into the autoclave under pressure at 140–150° C., and the autoclave is held for 150 minutes at this temperature. Cooling is followed by neutralization of the catalyst with acetic acid.

The resultant surfactant has a cloud point of 36° C., measured at 1% strength in water to DIN 53917. The surface tension is 30.4 mN/m, measured to DIN 53914, at a concentration of 1 g/l.

We claim:

1. An alcohol mixture substantively comprising alcohols having 13 or 15 carbon atoms, in which the proportion made up of all of the $C_{13}$ and $C_{15}$ alcohols is at least 95% by weight and where, based on the total alcohol content, at least 87% by weight of the alcohols have been selected among linear, 2-methyl-branched, and 2-ethyl-branched alcohols and where the mixture comprises from 40 to 60% by weight of linear alcohols, from 30 to 40% by weight of 2-methyl-branched alcohols and from 2 to 7% by weight of 2-ethyl-branched alcohols.

2. A mixture as claimed in claim 1, where the ratio of alcohols having 13 carbon atoms to alcohols having 15 carbon atoms is in the range from 90:10 to 50:50 by weight.

3. A process for preparing alcohol mixtures as claimed in claim 1, where:
   a) a monoolefin mixture is prepared, substantively comprising olefins having 12 or 14 carbon atoms and having linear α-olefins and from 5 to 20% by weight of olefins other than these, and
   b) the monoolefin mixture is hydroformylated by reaction with carbon mono oxide and hydrogen in the presence of a rhodium catalyst, and is hydrogenated.

4. A process as claimed in claim 3, where the monoolefin mixture has, based on the total olefin content, from 85 to 95% by weight of linear α-olefins, from 1 to 5% by weight of linear non-terminal olefins, from 5 to 10% by weight of viny-lidene-branched olefins, and, where appropriate, up to 5% by weight of other olefin isomers differing therefrom.

5. A process as claimed in claim 3, where the catalyst used in step b) has at least one ligand selected among compounds capable of forming complexes and having carbonyl, carboxylate, hydryde, sulfate, or nitrate groups, or having nitrogen-containing and/or phosphorus-containing groups, where the phosphorus-containing group has no more than one aryl radical with single bonding to the phosphorus atom.

6. A process as claimed in claim 5, where the catalyst used in step b) contains, as ligand, at least one phosphacyclohexane of the formula I or II

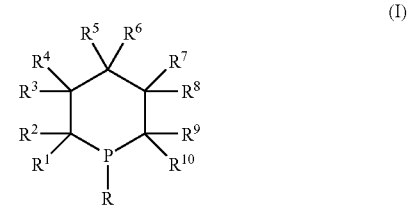

(I)

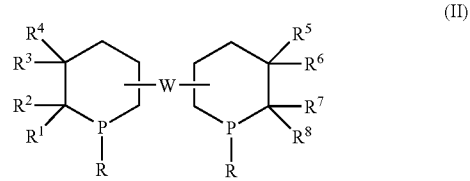

(II)

where
R is hydrogen, $C_{1-100}$-alkyl, cycloalkyl, heterocycloalkyl, $C_{7-20}$-aralkyl, $C_{7-20}$-alkaryl, $C_{6-12}$-aryl, hetaryl, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$)$_x$OR', W'(CH$_2$NR')$_x$R', W'(CH$_2$CH$_2$NR')$_x$R', W'((CH$_2$)$_4$O)$_x$R', or W'COR', where in formula II the radicals R may also, instead of or in addition to the group W, together form a bridge having from 1 to 20 carbon atoms, which may be a constituent of a cyclic or aromatic group and may have interruption by heteroatoms, and where in formula II the radicals R may also, instead of or in addition to the group W, together be a polyoxyalkylene bridge or polyalkyleneimine bridge having at least 21 carbon atoms, $R^1$ to $R^{10}$ independently of one another are hydrogen, $C_{1-20}$-alkyl, $C_{7-20}$-aralkyl, $C_{7-20}$-alkaryl, $C_{6-12}$-aryl, where one or more carbon atoms may have been replaced by heteroatoms, W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', W'((CH$_2$)$_4$O)$_x$R', W'halogen, W'NO$_2$, W'COR' or W'CN, where one or more hydrogen atoms in radicals R and $R^1$ to $R^{10}$ may have been replaced by fluorine, W and W' independently of one another are single bonds or bridges having from 1 to 20 carbon atoms, which may be a constituent of a cyclic or aromatic group and which may have interruption by heteroatoms.

7. A process as claimed in claim 6, where the compound of the formula I has been selected from compounds of the formula

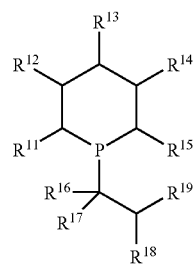

(III)

where:
$R^{11}$ to $R^{19}$, independently of one another, are hydrogen, $C_{1-20}$-alkyl, $C_{7-20}$-aralkyl, $C_{7-20}$-alkaryl, or $C_{6-12}$-aryl, where one or more carbon atoms may have replacement by heteroatoms, or W'COO$^-$M$^+$, W'SO$_3^-$M$^+$, W'PO$_3^{2-}$M$^+_2$, W'NR'$_3^+$X$^-$, W'OR', W'NR'$_2$, W'COOR', W'SR', W'(CHR'CH$_2$O)$_x$R', W'(CH$_2$NR')$_x$R', W'(CH$_2$CH$_2$NR')$_x$R', where any two vicinal radicals $R^{11}$ to $R^{15}$, and/or $R^{17}$ and $R_{18}$ and/or $R^{16}$ and $R^{17}$, and/or $R^{16}$ and $R^{19}$, and/or $R^{18}$ and $R^{19}$ may have bonding to give rings, W' is a single bond or bridge having from 1 to 20 carbon atoms, which may be a constituent of a cyclic or aromatic group, R' is a hydrogen or $C_{1-6}$-alkyl, M$^+$ is a cation, X$^-$ is an anion, and x is a number from 1 to 240, where one or more of the radicals $R^{11}$ to $R^{19}$ may have an additional triply bonded phosphorus-containing or nitrogen-containing group capable of coordination, and where $R^{18}$ may also be —W'—CR$^{20}$=CR$^{21}$R$^{22}$, where $R^{20}$, $R^{21}$, and $R^{22}$ are as defined above for R11 to $R^{19}$.

8. A process as claimed in claim 6, where the compounds of the formulae I and II have been selected from compounds of the formulae

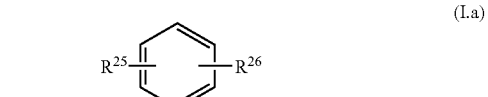

(I.a)

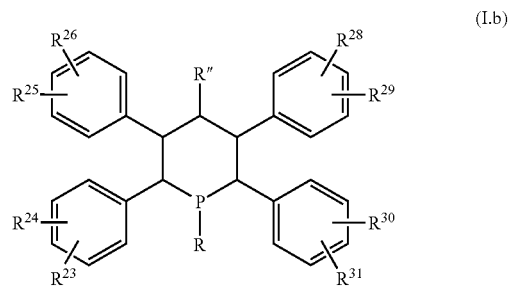

(I.b)

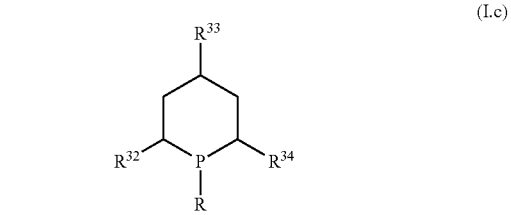

(I.c)

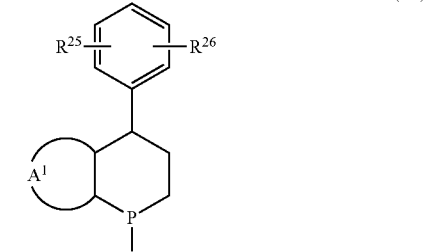

(I.d)

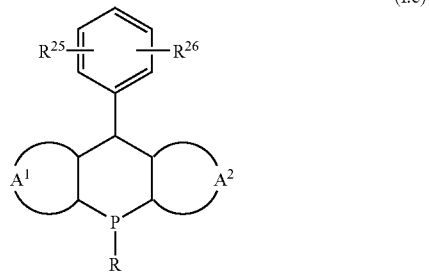

(I.e)

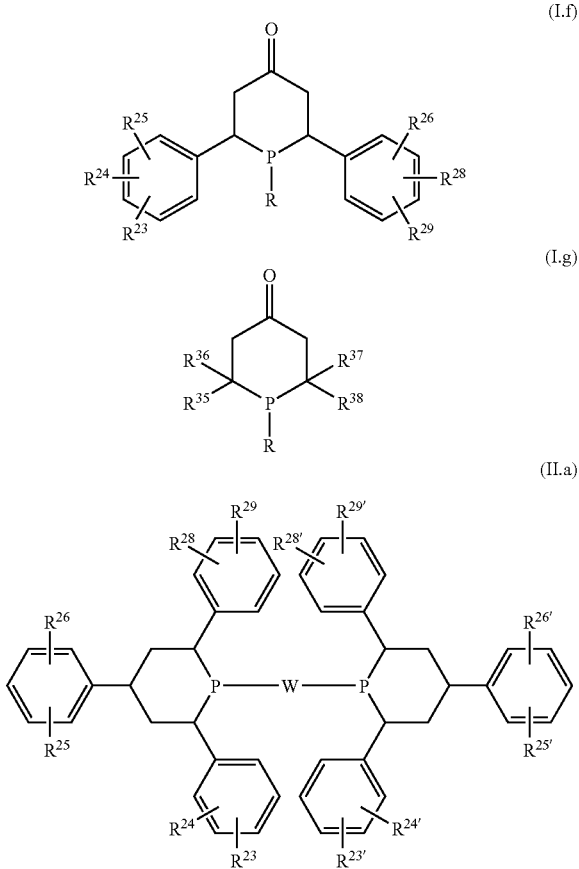

where
- R is $C_{1-20}$-alkyl, cycloalkyl, $C_{6-12}$-aryl, W'(CHR'$CH_2O)_xR'$, W'($(CH_2)_4O)_xR'$, or a polymer radical with number-average molecular weight in the range from 500 to 50 000, composed of ethylene and/or butadiene, where
- W' is a single bond or $C_{1-4}$-alkylene, and
- R' is hydrogen or $C_{1-20}$-alkyl,
- x is an integer from 1 to 240,
- $R^{23}$, $R^{23'}$, $R^{24}$, $R^{24'}$, $R^{25}$, $R^{25'}$, $R^{26}$, $R^{26'}$, $R^{28}$, $R^{28'}$, $R^{29}$, $R^{29'}$, $R^{30}$, and $R^{31}$, independently of one another, are hydrogen, alkyl, alkoxy, carboxy, carboxylate, trifluoromethyl, —$SO_3H$, sulfonate, $NE^1E^2$, or alkylene-$NE^1E^2$, where $E^1$ and $E^2$, independently of one another, are hydrogen, alkyl, or cycloalkyl,
- $R^{27}$ is hydrogen, alkyl, cycloalkyl, aryl, or aralkyl,
- $R^{32}$, $R^{33}$, $R^{34}$, $R^{35}$, $R^{36}$, $R^{37}$, and $R^{38}$, independently of one another, are alkyl or cycloalkyl,
- R" is hydrogen or phenyl,
- $A^1$ and $A^2$, together with those adjacent carbon atoms of the phosphacyclohexane to which they have been bonded, are an anellated ring system in each case having 1 or 2 further rings,
- W is a bridge having from 1 to 20 carbon atoms, which may have interruption by heteroatoms.

9. A process according to claim 5, where the catalyst used in step b) has, as ligand, at least one polyamine which is substantively non-water-soluble and has an average molecular weight of >1000 dalton, and has at least 10 nitrogen atoms.

10. A process for preparing functionalized alcohol mixtures, where an alcohol mixture as claimed in claim 1 is subjected to alkoxylation, glycosidation, sulfation, phosphation, alkoxylation followed by sulfation, or alkoxylation followed by phosphation.

11. A functionalized alcohol mixture obtainable by a process which comprises subjecting and alcohol mixture to alkoxylation, glycosidation, sulfation, phosphation, alkoxylation followed by sulfation, or alkoxytation followed by phosphation, wherein the alcohol mixture substantively comprises alcohols having 13 or 15 carbon atoms, in which the proportion made up of all of the $C_{13}$ and $C_{15}$ alcohols is at least 95% by weight and where, based on the total alcohol content, at least 87% by weight of the alcohols have been selected among linear, 2-methyl-branched, and 2-ethyl-branched alcohols and where the mixture comprises from 40 to 60% by weight of linear alcohols, from 30 to 40% by weight of 2-methyl-branched alcohols and from 2 to 7% by weight of 2-ethyl-branched alcohols.

12. A product selected from the group consisting of dispersants, paper auxiliaries, textile auxiliaries, leather auxiliaries, detergents, corrosion inhibitors, auxiliaries for dispersions, encrustation inhibitors, products for the metalworking industry, products for electroplating processes, surface-coatings, printing inks, pigment preparations, crop-protection formulations, products for water treatment, and products for plastics processing comprising the functionalized alcohol mixture defined in claim 11.

13. A mixture as claimed in claim 2, where the ratio of alcohols having 13 carbon atoms to alcohols having 15 carbon atoms is from 70:30 to 60:40 by weight.

14. A process according to claim 9, where the catalyst used in step b) has, as ligand, at least one derivatized polyamine or a polyethylene imine composed substantively of units of the formula (IV)

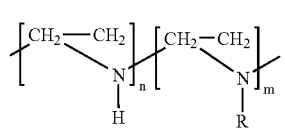

where m+n is at least 10 and the ratio m/(m+n) is from 0.01 to 1, and R is identical or different alkyl, cycloalkyl, aryl, aralkyl, or alkylcarbonyl radicals having up to 30 carbon atoms, or is hydroxyalkyl(poly)oxyalkylene radicals having up to 500 alkyleneoxy units.

15. The functionalized alcohol mixture defined in claim 11, where the ratio of alcohols having 13 carbon atoms to alcohols having 15 carbon atoms is in the range from 90:10 to 50:50 by weight.

16. The functionalized alcohol mixture defined in claim 15, where the ratio of alcohols having 13 carbon atoms to alcohols having 15 carbon atoms is from 70:30 to 60:40 by weight.

17. The product defined in claim 12, where the ratio of alcohols having 13 carbon atoms to alcohols having 15 carbon atoms of the functionalized alcohol mixture is in the range from 90:10 to 50:50 by weight.

18. The product defined in claim 17, where the ratio of alcohols having 13 carbon atoms to alcohols having 15 carbon atoms of the functionalized alcohol mixture is from 70:30 to 60:40 by weight.

* * * * *

UNITED STATES PATENT AND TRADEMARK OFFICE
CERTIFICATE OF CORRECTION

PATENT NO. : 7,183,446 B2
APPLICATION NO. : 10/311583
DATED : February 27, 2007
INVENTOR(S) : Zeller et al.

It is certified that error appears in the above-identified patent and that said Letters Patent is hereby corrected as shown below:

Claim 4, col. 28, indicated line 38:
"viny-lidene-branched" should read --vinylidene-branched--

Claim 7, col. 30, line 5:
"R11" should read --$R^{11}$--

Claim 9, col. 31, indicated line 55:
"one! another" should read --one another--

Claim 11, col. 32, indicated line 7:
"subjecting and alcohol" should read --subjecting an alcohol--

Claim 14, col. 32, at indicated line 40:

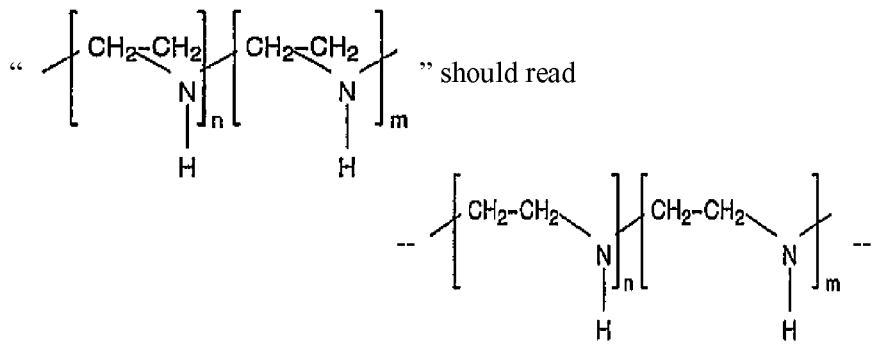 should read

Signed and Sealed this

Tenth Day of July, 2007

JON W. DUDAS
*Director of the United States Patent and Trademark Office*